United States Patent
Son et al.

(10) Patent No.: US 11,203,019 B2
(45) Date of Patent: Dec. 21, 2021

(54) METHOD AND SYSTEM FOR TEMPERATURE MONITORING OF A BIOCHEMICAL REACTION VESSEL

(71) Applicant: Kryptos Biotechnologies, Inc., Hayward, CA (US)

(72) Inventors: Jun Ho Son, Albany, CA (US); Austin So, Pleasanton, CA (US)

(73) Assignee: Kryptos Biotechnologies, Inc., Hayward, CA (US)

( * ) Notice: Subject to any disclaimer, the term of this patent is extended or adjusted under 35 U.S.C. 154(b) by 184 days.

(21) Appl. No.: 16/654,462

(22) Filed: Oct. 16, 2019

(65) Prior Publication Data

US 2020/0114362 A1   Apr. 16, 2020

Related U.S. Application Data

(60) Provisional application No. 62/746,488, filed on Oct. 16, 2018, provisional application No. 62/746,492, filed on Oct. 16, 2018.

(51) Int. Cl.
*B01L 7/00* (2006.01)
*B01J 19/00* (2006.01)
(Continued)

(52) U.S. Cl.
CPC .............. *B01L 7/52* (2013.01); *B01J 19/0013* (2013.01); *B01J 19/08* (2013.01); *C12M 31/08* (2013.01);
(Continued)

(58) Field of Classification Search
CPC .. B01L 7/52; B01L 3/50821; B01L 2200/147; B01L 2300/0829;
(Continued)

(56) References Cited

U.S. PATENT DOCUMENTS 5,786,182 A   7/1998 Catanzariti et al.
7,081,226 B1  7/2006 Wittwer et al.
(Continued)

FOREIGN PATENT DOCUMENTS

WO   WO-2017019768 A1 * 2/2017 ............. C12Q 1/686

OTHER PUBLICATIONS

International Patent Application No. PCT/US2019/056560, "International Search Report and Written Opinion", dated Feb. 21, 2020, 13 pages.

(Continued)

*Primary Examiner* — Michael L Hobbs
(74) *Attorney, Agent, or Firm* — Kilpatrick Townsend & Stockton LLP

(57) ABSTRACT

Embodiments include a reaction vessel having a first reaction chamber filled with a first material; a first light absorbing region adhered to an interior-facing surface of the first reaction chamber; a second reaction chamber filled with a second material; a second light absorbing region adhered to an interior-facing surface of the second reaction chamber; a temperature sensor disposed within the second reaction chamber; and one or more energy sources configured to direct light at the first light absorbing region and the second light absorbing region. A processor may be employed to determine a first temperature of the first material from a second temperature of the second material measured by the temperature sensor. Methods of manufacturing such a reaction vessel are also disclosed.

13 Claims, 26 Drawing Sheets

(51) Int. Cl.
  *C12M 1/34* (2006.01)
  *B01J 19/08* (2006.01)
  *C12M 1/00* (2006.01)

(52) U.S. Cl.
  CPC .... *C12M 41/12* (2013.01); *B01J 2219/00144* (2013.01); *B01J 2219/00146* (2013.01); *B01J 2219/00761* (2013.01); *B01L 2200/147* (2013.01); *B01L 2300/0825* (2013.01); *B01L 2300/0829* (2013.01); *B01L 2300/0851* (2013.01); *B01L 2300/12* (2013.01); *B01L 2300/168* (2013.01); *B01L 2300/1838* (2013.01); *B01L 2300/1861* (2013.01)

(58) Field of Classification Search
  CPC ........... B01L 2300/12; B01L 2300/168; B01L 2300/0851; B01L 2300/0825; B01L 2300/1838; B01L 2300/1861; B01L 2300/0654; B01L 2300/1883; B01L 2300/0819; B01J 9/0013; B01J 9/08; B01J 2219/00146; B01J 2219/00761; C12M 31/08; C12M 41/12
  See application file for complete search history.

(56) References Cited

U.S. PATENT DOCUMENTS

| | | | |
|---|---|---|---|
| 2013/0137169 A1* | 5/2013 | Kojima | G01N 21/6486 435/289.1 |
| 2016/0265032 A1 | 9/2016 | Sethi et al. | |
| 2018/0236451 A1 | 8/2018 | Lee et al. | |
| 2018/0361379 A1* | 12/2018 | Biro | B01L 7/52 |

OTHER PUBLICATIONS

International Patent Application No. PCT/US2019/056560, "Invitation to Pay Additional Fees and, Where Applicable, Protest Fee", Dec. 26, 2019, 2 pages.

PCT/US2019/056560, "International Preliminary Report on Patentability", Apr. 29, 2021, 9 pages.

* cited by examiner

|  | One-sided heating | | Dual-sided heating | |
| --- | --- | --- | --- | --- |
|  | Heating (sec) | Cooling (sec) | Heating (sec) | Cooling (sec) |
| 1st cycle (room temperature to 95 °C) | 27.43 | 7.47 | 6.81 | 4.71 |
| 2nd cycle (65 °C to 95 °C) | 14.23 | 7.81 | 3.14 | 5.23 |
| 3rd cycle (65 °C to 95 °C) | 14.1 | 7.89 | 2.9 | 5.24 |

700

| |
|---|
| Introduce a reagent into a first reaction chamber, wherein the first reaction chamber comprises a first light absorbing layer and a second light absorbing layer, the first and second light absorbing layers having an inner surface that is oriented toward an interior of the first reaction chamber and an outer surface that is oriented away from the interior of the first reaction chamber |

710

↓

| |
|---|
| Direct, by a first energy source, a first light toward the outer surface of the first light absorbing layer so as to heat the first light absorbing layer |

720

↓

| |
|---|
| Direct, by a second energy source, a second light toward the outer surface of the second light absorbing layer so as to heat the second light absorbing layer |

730

↓

| |
|---|
| Cause heat from the first and second light absorbing layers to be transferred to the reagent. |

METHOD AND SYSTEM FOR TEMPERATURE MONITORING OF A BIOCHEMICAL REACTION VESSEL

CROSS-REFERENCE TO RELATED APPLICATIONS

This application claims priority to U.S. Provisional Patent Application No. 62/746,488, filed Oct. 16, 2018, entitled "METHOD AND SYSTEM FOR TEMPERATURE MONITORING OF A BIOCHEMICAL VESSEL," and U.S. Provisional Patent Application No. 62/746,492, filed Oct. 16, 2018, entitled "METHOD AND SYSTEM FOR REACTION VESSEL WITH MULTISIDED ENERGY SOURCES," the disclosures of which are hereby incorporated by reference in their entirety for all purposes.

The following regular U.S. patent applications (including this one) are being filed concurrently, and the entire disclosure of the other applications are incorporated by reference into this application for all purposes:
 application Ser. No. 16/654,484, filed Oct. 16, 2018, entitled "METHOD AND SYSTEM FOR REACTION VESSEL WITH MULTISIDED ENERGY SOURCES"; and
 application Ser. No. 16/654,462, filed Oct. 16, 2018, entitled "METHOD AND SYSTEM FOR TEMPERATURE MONITORING OF A BIOCHEMICAL REACTION VESSEL".

BACKGROUND OF THE INVENTION

Reaction vessels are often used to perform various operations on DNA strands that can include operations such as polymerase chain reaction (PCR) and DNA sequencing. Polymerase chain reaction (PCR) has become an essential technique in the fields of clinical laboratories, agricultural science, environmental science, and forensic science. PCR requires thermal cycling, or repeated temperature changes between two or three discrete temperatures to amplify specific nucleic acid target sequences. To achieve such thermal cycling, conventional bench-top thermal cyclers generally use a metal heating block powered by Peltier elements. Unfortunately, this method of thermally cycling the materials within the reaction vessels can be slower than desired. For these reasons, alternate means that improve the speed and/or reliability of the thermal cycling are desirable.

SUMMARY OF THE INVENTION

This disclosure relates to methods and apparatus suitable for use in reactions, assays, or experiments where temperature control or monitoring is desired. A number of reaction vessels and systems are disclosed, along with methods of operating the reaction vessels and systems, and methods of manufacturing the reaction vessels.

In some embodiments, a reaction vessel system may include a reaction vessel comprising: a housing; a first reaction chamber defined by opposing first and second interior-facing surfaces of the housing; a first light absorbing layer conforming to the first interior-facing surface of the housing; and a second light absorbing layer conforming to the second interior-facing surface of the housing. The reaction vessel system may further include a first energy source configured to direct light through the housing at the first light absorbing layer; and a second energy source configured to direct light through the housing at the second light absorbing layer. In some embodiments, the housing is configured to be disposed between the first energy source and the second energy source when in use. In some embodiments, the first light absorbing layer and the second light absorbing layer have a same thickness and composition.

In some embodiments, the first and second light absorbing layers each comprise a metallic film formed on respective first and second interior-facing surfaces of the housing. In some embodiments, the metallic film is formed on, deposited on, adhered to, or otherwise disposed on the first and second interior-facing surfaces of the housing.

In some embodiments, at least a portion of the housing is optically transparent to wavelengths of light emitted by the first and second energy sources. In some embodiments, the first energy source is a light emitting diode configured to emit visible light. In some embodiments, the first energy source is a light emitting diode configured to emit infrared light.

In some embodiments, the reaction vessel system may include an excitation light source assembly and an emission detecting sensor assembly, wherein the excitation light source assembly comprises an excitation light source configured to direct an excitation light configured to cause a fluorescent marker within the first reaction chamber to emit a fluorescent light, and wherein the emission detecting sensor assembly comprises an emission sensor configured to detect the emitted fluorescent light. The reaction vessel system may include an emission filter disposed between the first reaction chamber and the emission sensor, wherein the emission filter is configured to allow light of one or more first wavelengths corresponding to the emitted fluorescent light, and filter out light of one or more second wavelengths, wherein the one or more first wavelengths are different from the one or more second wavelengths. The reaction vessel system may include an excitation filter disposed between the first reaction chamber and the excitation light source, wherein the excitation filter is configured to allow light of one or more third wavelengths configured to excite the fluorescent marker, and filter out light of one or more fourth wavelengths, wherein the one or more third wavelengths are different from the one or more fourth wavelengths.

In some embodiments, the first and second energy sources further comprise optical fibers that carry the emitted fluorescent light at least a portion of a distance between the energy sources and the housing. In some embodiments, the first energy source comprises a chip on board LED (COB LED), wherein the COB LED comprises a plurality of LED chips that are configured to be individually controllable.

In some embodiments, the reaction vessel system includes a second reaction chamber; a third energy source configured to direct light through the housing at the first light absorbing layer adjacent to the second reaction chamber; and a fourth energy source configured to direct light through the housing at the second light absorbing layer adjacent to the second reaction chamber; wherein the first, second, third, and fourth energy sources are individually controllable. In some embodiments, the first light absorbing layer comprises a first discrete region associated with the first reaction chamber and a second discrete region associated with the second reaction chamber, and wherein the first energy source is configured to direct light at the first discrete region and the third energy source is configured to direct light at the second discrete region.

In some embodiments, the first energy source and the second energy source are optical fibers coupled to a single precursor energy source, wherein energy from the single precursor energy source is divided between the first energy source and the second energy source.

In some embodiments, the first and second light absorbing layers having an inner surface that is oriented toward an interior of the first reaction chamber and an outer surface that is oriented away from the interior of the first reaction chamber, and wherein the first and second energy sources are configured to direct light at the outer surfaces of the first and second light absorbing layers A method of operating a temperature-controlled reaction vessel system is disclosed, wherein the method includes: introducing a reagent into a first reaction chamber, wherein the first reaction chamber comprises a first light absorbing layer and a second light absorbing layer, the first and second light absorbing layers having an inner surface that is oriented toward an interior of the first reaction chamber and an outer surface that is oriented away from the interior of the first reaction chamber; direct, by a first energy source, a first light toward the outer surface of the first light absorbing layer so as to heat the first light absorbing layer; direct, by a second energy source, a second light toward the outer surface of the second light absorbing layer so as to heat the second light absorbing layer; and causing heat from the first and second light absorbing layers to be transferred to the reagent.

In some embodiments, the method includes introducing a reagent into a second reaction chamber; causing a third energy source to direct a third light toward an outer surface of the first light absorbing layer adjacent to a second reaction chamber; and causing a fourth energy source to direct a fourth light toward an outer surface of the second light absorbing layer adjacent to the second reaction chamber.

In some embodiments, the first light absorbing layer comprises a first discrete region associated with the first reaction chamber and a second discrete region associated with the second reaction chamber, and wherein the first light is directed toward the first discrete region and the third light is directed toward the second discrete region. In some embodiments, the second light absorbing layer comprises a first discrete region associated with the first reaction chamber and a second discrete region associated with the second reaction chamber, and wherein the second light is directed toward the first discrete region and the fourth light is directed toward the second discrete region.

In some embodiments, the method includes directing an excitation light from an excitation light source toward the first reaction chamber, wherein the excitation light is configured to cause a fluorescent marker within the first reaction chamber to emit a fluorescent light; and detecting, by an emission detecting sensor assembly, the emitted fluorescent light. The method may include filtering light reaching the emission detecting sensor assembly with an emission filter disposed between the first reaction chamber and the emission sensor, wherein the filtering comprises allowing light of one or more first wavelengths corresponding to the emitted fluorescent light, and filtering out light of one or more second wavelengths, wherein the one or more first wavelengths are different from the one or more second wavelengths. The method may include filtering light from the excitation light source with an excitation filter disposed between the first reaction chamber and the excitation light source, wherein the filtering comprises allowing light of one or more third wavelengths configured to excite the fluorescent marker, and filtering out light of one or more fourth wavelengths, wherein the one or more third wavelengths are different from the one or more fourth wavelengths.

In some embodiments, the method may include detecting, by a temperature sensor, a temperature associated with the first reaction chamber; and logging, within a memory, a value indicating the detected temperature and a value corresponding to the emitted fluorescent light (e.g., a value quantifying the amount of emitted fluorescent light, or simply indicating whether or not a threshold amount of fluorescent light was emitted).

In some embodiments, a reaction vessel system may include a first chamber filled with a first material; a first light absorbing region adhered to a first interior-facing surface of the first chamber; a second chamber filled with a second material, wherein the second material is different from the first material; a second light absorbing region adhered to a first interior-facing surface of the second chamber; a temperature sensor disposed within the second chamber for measuring a second temperature; one or more energy sources configured to direct light at the first light absorbing region and the second light absorbing region; and a processor configured to determine a first temperature of the first chamber based on the second temperature of the second chamber measured by the temperature sensor.

In some embodiments, the reaction vessel system includes one or more energy attenuating features configured to reduce an amount of energy transmitted to the second light absorbing region. In some embodiments, the one or more energy attenuating features are selected from a group consisting of a light diffusing layer, a light reflecting layer, a filter layer, or a light blocking layer.

In some embodiments, the one or more energy sources comprise a first energy source configured to direct light at the first light absorbing region and a second energy source configured to direct light at the second light absorbing region.

In some embodiments, the first material has a different specific heat than the second material. In some embodiments, the second material is a polymeric material, an adhesive material, or any other suitable material.

In some embodiments, the reaction vessel system includes an excitation light source assembly and an emission detecting sensor assembly, wherein the excitation light source assembly comprises an excitation light source configured to direct an excitation light configured to cause a fluorescent marker within the first chamber to emit a fluorescent light, and wherein the emission detecting sensor assembly comprises an emission sensor configured to detect the emitted fluorescent light.

In some embodiments, the reaction vessel system includes a third light absorbing region adhered to a second interior-facing surface of the first chamber, wherein the second interior-facing surface of the first chamber opposes the first interior-facing surface of the first chamber; a fourth light absorbing region adhered to a second interior-facing surface of the second chamber, wherein the second interior-facing surface of the first chamber opposes the first interior-facing surface of the first chamber; and one or more additional energy sources configured to direct light at the third light absorbing region and the fourth light absorbing region.

In some embodiments, a reaction vessel may include a first chamber filled with a first material; a first light absorbing region adhered to a first interior-facing surface of the first reaction chamber; a second chamber filled with a second material, wherein the second material is different from the first material; a second light absorbing region adhered to a first interior-facing surface of the second chamber; a temperature sensor disposed within the second chamber for measuring a second temperature; and a connector for coupling the temperature sensor to a processor, wherein the temperature sensor is configured to send a signal corresponding to the second temperature to the processor for determining a correlated first temperature corresponding to the first chamber. The first light absorbing region and the second light absorbing region may be configured to absorb energy from one or more light sources. In some embodiments, reaction vessel may include one or more energy attenuating features configured to reduce an amount of energy transmitted to the second light absorbing region.

In some embodiments, a method of monitoring a reaction chamber temperature is disclosed. The method may include measuring a first temperature of a temperature-monitoring chamber associated with a reaction vessel, wherein the temperature-monitoring chamber is filled with a potting material; transmitting a signal corresponding to the first temperature to a processor; determining, by the processor, a first temperature value corresponding to the first temperature; and estimating, based on the first temperature value, a second temperature value associated with a reaction chamber. In some embodiments, the temperature-monitoring chamber is housed in a module that is separated from the reaction vessel.

In some embodiments, the estimating comprises accessing a lookup table correlating a plurality of temperature values corresponding to the temperature-monitoring chamber with a plurality of temperature values corresponding to the reaction chamber. In some embodiments, the estimating comprises applying a function to the first temperature value to generate the second temperature value.

In some embodiments, the potting material has a different specific heat than a material within the reaction chamber.

In some embodiments, the method includes adjusting, based on the first temperature, a power level of an energy source configured to heat the reaction chamber.

In some embodiments, a method of manufacturing a reaction vessel is disclosed. The method may include forming a first portion of a reaction vessel housing, the first portion of the reaction vessel housing having a plurality of depressions; forming a second portion of the reaction vessel housing; securing the first and second portions of the reaction vessel housing to each other, such that the depressions at least in part define a plurality of chambers, the plurality of chambers comprising a reaction chamber and a temperature-monitoring chamber; introducing a liquid material into the temperature-monitoring chamber; placing a temperature sensor at a desired position within the temperature-monitoring chamber; and causing the liquid material to solidify within the temperature-monitoring chamber.

In some embodiments, the liquid material is a polymeric material. In some embodiments, the liquid material is a silane-modified polymer. In these examples, the liquid material may be caused to solidify by directing UV energy at the temperature-monitoring chamber.

In some embodiments, the second portion of the reaction vessel housing has one or more depressions.

In some embodiments, reaction vessel may include a housing having a plurality of walls that define a reaction chamber filled with a solution (e.g., one or more chemicals or biologicals, reagents); a light absorbing region adhered to an interior-facing surface of a first wall of the plurality of walls defining the reaction chamber; a temperature sensor embedded within a second one of the plurality of walls defining the reaction chamber; an energy source configured to direct light through the reaction chambers at the light absorbing region. In some embodiments, a temperature of the solution may be determined (e.g., by a processor) based on a measurement made by the temperature sensor. In some embodiments, the first wall is different from the second wall.

Other aspects and advantages of the invention will become apparent from the following detailed description taken in conjunction with the accompanying drawings which illustrate, by way of example, the principles of the described embodiments.

BRIEF DESCRIPTION OF THE DRAWINGS

The disclosure will be readily understood by the following detailed description in conjunction with the accompanying drawings, wherein like reference numerals designate like structural elements, and in which:

FIG. 7 illustrates an example method for operating a temperature-controlled reaction vessel system;

DETAILED DESCRIPTION OF THE INVENTION

Figure 1A:
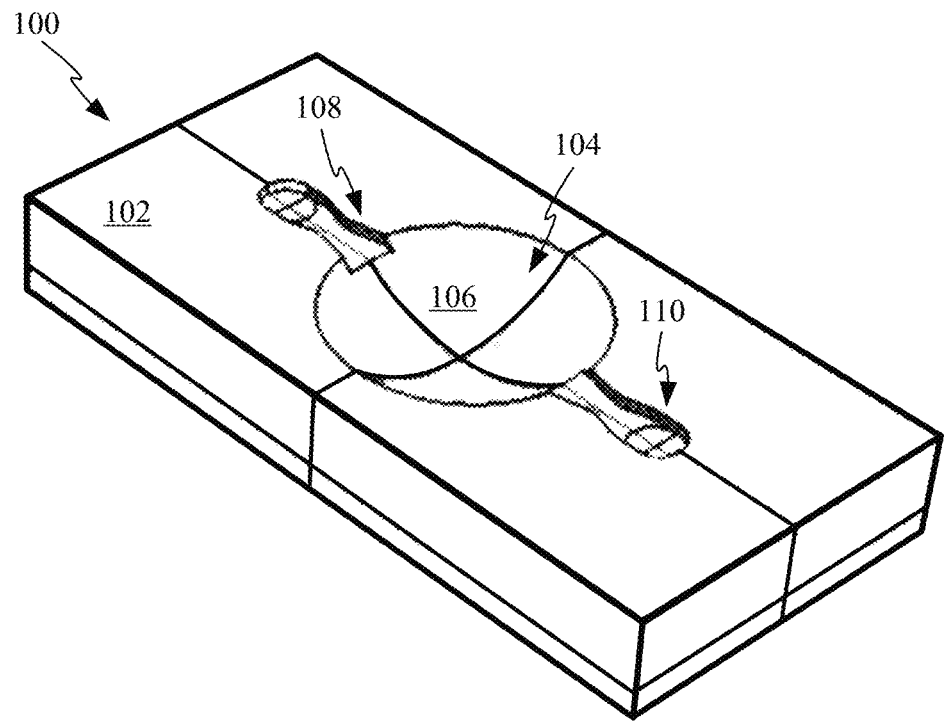
FIG. 1A shows an exemplary reaction vessel suitable for use with the described embodiments.

In the following detailed description, references are made to the accompanying drawings, which form a part of the description and in which are shown, by way of illustration, specific embodiments in accordance with the described embodiments. Although these embodiments are described in sufficient detail to enable one skilled in the art to practice the described embodiments, it is understood that these examples are not limiting; such that other embodiments may be used, and changes may be made without departing from the spirit and scope of the described embodiments.

Microfluidics systems or devices have widespread use in chemistry and biology. In such devices, fluids are transported, mixed, separated or otherwise processed. In many microfluidics devices, various applications rely on passive fluid control using capillary forces. In other applications, external actuation means (e.g., rotary drives) are used for the directed transport of fluids. "Active microfluidics" refers to the defined manipulation of the working fluid by active (micro) components such as micropumps or microvalves. Micropumps supply fluids in a continuous manner or are used for dosing. Microvalves determine the flow direction or the mode of movement of pumped liquids. Processes that are normally carried out in a laboratory can be miniaturized on a single chip in order to enhance efficiency and mobility as well to reduce sample and reagent volumes. Microfluidic structures can include micropneumatic systems, i.e., microsystems for the handling of off-chip fluids (liquid pumps, gas valves, etc.), and microfluidic structures for the on-chip handling of nanoliter (nl) and picoliter (pl) volumes (Nguyen and Wereley, Fundamentals and Applications of Microfluidics, Artech House, 2006).

Advances in microfluidics technology are revolutionizing molecular biology procedures for enzymatic analysis (e.g., glucose and lactate assays), DNA analysis (e.g., polymerase chain reaction and high-throughput sequencing), and proteomics. Microfluidic biochips integrate assay operations such as detection, as well as sample pre-treatment and sample preparation on one chip (Herold and Rasooly, editors, Lab-on-a-Chip Technology: Fabrication and Microfluidics, Caister Academic Press, 2009; Herold and Rasooly, editors, Lab-on-a-Chip Technology: Biomolecular Separation and Analysis, Caister Academic Press, 2009). An emerging application area for biochips is clinical pathology, especially the immediate point-of-care diagnosis of diseases. In addition, some microfluidics-based devices are capable of continuous sampling and real-time testing of air/water samples for biochemical toxins and other dangerous pathogens.

Many types of microfluidic architectures are currently in use and include open microfluidics, continuous-flow microfluidics, droplet-based microfluidics, digital microfluidics, paper-based microfluidics and DNA chips (microarrays).

In open microfluidics, at least one boundary of the system is removed, exposing the fluid to air or another interface (i.e., liquid) (Berthier et al., Open microfluidics, Hoboken, N.J.: Wiley, Scrivener Publishing, 2016; Pfohl et al., Chem Phys Chem. 4:1291-1298, 2003; Kaigala et al., Angewandte Chemie International Edition. 51:11224-11240, 2012). Advantages of open microfluidics include accessibility to the flowing liquid for intervention, larger liquid-gas surface area, and minimized bubble formation (Berthier et al., Open microfluidics, Hoboken, N.J.: Wiley, Scrivener Publishing, 2016; Kaigala et al., Ange. Chemie Int. Ed. 51:11224-11240, 2012; Li et al., Lab on a Chip 17: 1436-1441). Another advantage of open microfluidics is the ability to integrate open systems with surface-tension driven fluid flow, which eliminates the need for external pumping methods such as peristaltic or syringe pumps (Casavant et al., Proc. Nat. Acad. Sci. USA 110:10111-10116, 2013). Open microfluidic devices are also inexpensive to fabricate by milling, thermoforming, and hot embossing (Guckenberger et al., Lab on a Chip, 15: 2364-2378, 2015; Truckenmuller et al., J. Micromechanics and Microengineering, 12: 375-379, 2002; Jeon et al., Biomed. Microdevices 13: 325-333, 2010; Young et al., Anal. Chem. 83:1408-1417, 2011). In addition, open microfluidics eliminates the need to glue or bond a cover for devices which could be detrimental for capillary flows. Examples of open microfluidics include open-channel microfluidics, rail-based microfluidics, paper-based, and thread-based microfluidics (Berthier et al., Open microfluidics, Hoboken, N.J.: Wiley, Scrivener Publishing, 2016; Casavant et al., Proc. Nat. Acad. Sci. USA 110:10111-10116, 2013; Bouaidat et al., Lab on a Chip 5: 827, 2005).

Continuous flow microfluidics are based on the manipulation of continuous liquid flow through microfabricated channels (Nguyen et al., Micromachines 8:186, 2017; Antfolk and Laurell, Anal. Chim. Acta 965:9-35, 2017). Actuation of liquid flow is implemented either by external pressure sources, external mechanical pumps, integrated mechanical micropumps, or by combinations of capillary forces and electrokinetic mechanisms. Continuous-flow devices are useful for many well-defined and simple biochemical applications and for certain tasks such as chemical separations, but they are less suitable for tasks requiring a high degree of flexibility or fluid manipulations. Process monitoring capabilities in continuous-flow systems can be achieved with highly sensitive microfluidic flow sensors based on micro-electro-mechanical systems (MEMS) technology, which offers resolutions down to the nanoliter range.

Droplet-based microfluidics manipulates discrete volumes of fluids in immiscible phases with low Reynolds number and laminar flow regimes (see reviews at Shembekar et al., Lab on a Chip 8:1314-1331, 2016; Zhao-Miao et al., Chinese J. Anal. Chem. 45:282-296, 2017. Microdroplets allow for the manipulation of miniature volumes (μl to fl) of fluids conveniently, provide good mixing, encapsulation, sorting, and sensing, and are suitable for high throughput applications (Chokkalingam et al., Lab on a Chip 13:4740-4744, 2013).

Alternatives to closed-channel continuous-flow systems include open structures, wherein discrete, independently controllable droplets are manipulated on a substrate using electrowetting. By using discrete unit-volume droplets (Chokkalingam et al., Appl. Physics Lett. 93:254101, 2008), a microfluidic function can be reduced to a set of repeated basic operations, i.e., moving one unit of fluid over one unit of distance. This "digitization" method facilitates the use of a hierarchical, cell-based approach for microfluidic biochip design. Therefore, digital microfluidics offers a flexible, scalable system architecture as well as high fault-tolerance. Moreover, because each droplet can be controlled independently, these systems also have dynamic reconfigurability, whereby groups of unit cells in a microfluidic array can be reconfigured to change their functionality during the concurrent execution of a set of bioassays. Alternatively, droplets can be manipulated in confined microfluidic channels. One common actuation method for digital microfluidics is electrowetting-on-dielectric (EWOD) (reviewed in Nelson and Kim, J. Adhesion Sci. Tech., 26:12-17, 1747-1771, 2012). Many lab-on-a-chip applications have been demonstrated within the digital microfluidics paradigm using electrowetting. However, recently other techniques for droplet manipulation have also been demonstrated using magnetic force (Zhang and Nguyen, Lab on a Chip 17.6: 994-1008, 2017), surface acoustic waves, optoelectrowetting, mechanical actuation (Shemesh et al., Biomed. Microdevices 12:907-914, 2010), etc.

Paper-based microfluidics (Berthier et al., Open Microfluidics, John Wiley & Sons, Inc. pp. 229-256, 2016) rely on the phenomenon of capillary penetration in porous media. In order to tune fluid penetration in porous substrates such as paper in two and three dimensions, the pore structure, wettability and geometry of the microfluidic devices can be controlled, while the viscosity and evaporation rate of the liquid play a further significant role. Many such devices feature hydrophobic barriers on hydrophilic paper that passively transport aqueous solutions to outlets where biological reactions take place (Galindo-Rosales, Complex Fluid-Flows in Microfluidics, Springer, 2017).

Early biochips were based on the idea of a DNA microarray, e.g., the GeneChip DNA array from Affymetrix, which is a piece of glass, plastic or silicon substrate on which DNA molecules (probes) are affixed in an array. Similar to a DNA microarray, a protein array is an array in which a multitude of different capture agents, e.g., monoclonal antibodies, are deposited on a chip surface. The capture agents are used to determine the presence and/or amount of proteins in a biological sample, e.g., blood. For a review, see, e.g., Bumgarner, Curr. Protoc. Mol. Biol. 101:22.1.1-22.1.11, 2013.

In addition to microarrays, biochips have been designed for two-dimensional electrophoresis, transcriptome analysis, and PCR amplification. Other applications include various electrophoresis and liquid chromatography applications for proteins and DNA, cell separation, in particular, blood cell separation, protein analysis, cell manipulation and analysis including cell viability analysis and microorganism capturing.

Reaction vessels are often used to perform various types of operations on DNA strands that include polymerase chain reactions (PCR) and DNA sequencing. Reaction vessels can incorporate one or more of the microfluidics architectures listed above but it should be appreciated that reaction vessels can be larger than microfluidics devices and for that reason may not incorporate any of the microfluidics architectures described above. Operations of the reaction vessels often include the need to make rapid changes in temperature within the reaction vessel. For example, in a PCR operation solution containing DNA strands is positioned within a reaction chamber defined by the reaction vessel. A heating element is used to thermally cycle the solution in order to breakdown and/or build up various different types of DNA. Unfortunately, conventional means of thermally cycling the solution are often slower than desired and not capable of varying a temperature of specific regions of a reaction chamber within the reaction vessel.

One solution to this problem is to position a light absorbing layer within the reaction chamber of the reaction vessel with light absorption characteristics (e.g., allowing absorption of between 50 and 90% of the photonic energy in any light absorbed by the light absorbing layer). An energy source can be configured to direct light at the light absorbing layer, which efficiently absorbs energy from photons of the light directed at the light absorbing layer. The absorption of the photonic energy may rapidly increase the temperature of the light absorbing layer. This energy received by the light absorbing layer may then be transferred to a solution within the reaction chamber by thermal conduction and/or convection.

In some embodiments, a light absorbing layer extends across both upper and lower surfaces of a reaction chamber. This configuration allows the light absorbing layer to have a larger area across which light can be received by one or more energy sources. For example, the energy sources can be positioned both above and below the reaction chamber. While the light absorbing layer could be extended across any of the walls forming the reaction chamber, extending the light absorbing layer across both the upper and lower surface will generally double an amount of material introducing heat into a solution (e.g., one or more reagents) within the reaction chamber. The described configuration also reduces a thermal gradient formed within the reaction chamber since the solution can be heated from both the upper and lower surfaces, making the center of the reaction chamber likely to be the slowest in increasing in temperature.

In some embodiments, an array of reaction vessels or reaction chambers can be grouped together and a temperature-monitoring module can replace one of the reaction vessels or reaction chambers in order to accurately monitor a temperature of the reaction vessels or reaction chambers making up the array. The temperature-monitoring module can have a similar size and shape to the reaction vessels or reaction chambers it replaces. The temperature-monitoring module can include a temperature sensor such as, e.g., a thermocouple, thermistor or resistance temperature detector (RTD). The temperature sensor can be suspended in a material having a specific heat similar to a specific heat of the solution within the other reaction vessels or reaction chambers. In this way, the material within the temperature-monitoring module can closely match the temperature within the other reaction vessels or reaction chambers.

One benefit of this configuration is that this alleviates the need to suspend a temperature sensor within reaction vessels or reaction chambers being used to perform various chemical/biological operations. The material can also be a polymeric material that is able to maintain the temperature sensor at a central position within the reaction vessel or reaction chamber. In some embodiments, this can be preferable to placing the temperature sensor within an active reaction vessel or reaction chamber where the temperature might be secured directly to a light absorbing layer that could result in readings from the temperature sensor not reflecting the average temperature within the reaction vessel or reaction chamber.

These and other embodiments are discussed below; however, those skilled in the art will readily appreciate that the detailed description given herein with respect to these figures is for explanatory purposes only and should not be construed as limiting.

FIG. 1A shows a perspective view of an exemplary reaction vessel 100 suitable for use with the described embodiments. In particular, reaction vessel 100 includes a housing component 102 formed from an optically transparent material that defines a reaction chamber 104. While reaction chamber 104 is depicted as having a substantially circular geometry it should be appreciated that the depicted shape of reaction chamber 104 should not be construed as limiting and other shapes such as oval, rhombic and rectangular are also possible. In some embodiments, the optically transparent material forming housing component 102 can be optically transparent to only those wavelengths of light that are used to heat reaction vessel 100. For example, the optically transparent material could be optically transparent to only select visible, infrared or ultraviolet frequencies of light. Reaction chamber 104 can be closed by a second housing component (not depicted) that encloses a liquid being heated within reaction chamber 104. In this way, DNA strands in a liquid solution within reaction chamber 104 can undergo rapid thermal cycles and at least a portion of any vaporized portion of the solution can subsequently condense back into the solution between the thermal cycles or after the thermal cycling is complete. A light absorbing layer 106 can be formed on, deposited on, adhered to, or otherwise disposed on an interior-facing surface of reaction chamber 104. Light absorbing layer 106 has good light absorbing properties and can be in direct contact with any liquid disposed within reaction chamber 104. For example, light absorbing layer 106 can be configured to absorb about 50-90% of the photonic energy incident to light absorbing layer 106. In some embodiments, light absorbing layer 106 can be a metal film formed from elemental gold, chromium, titanium, germanium or a gold alloy such as, e.g., gold-germanium, gold-chromium, gold-titanium, gold-chromium-germanium and gold-titanium-germanium. In some embodiments, light absorbing layer 106 can be a multilayer metal film formed from elemental gold, chromium, titanium, germanium or a gold alloy such as, e.g., gold-germanium, gold-chromium, gold-titanium, gold-chromium-germanium and gold-titanium-germanium. Light absorbing layer 106 can have a thickness of about 5 nm-200 nm. Housing component 102 also defines inlet channel 108 and outlet channel 110, which can be used to cycle various chemicals, primers, DNA strands and other biological materials into and out of reaction chamber 104. In some embodiments, housing component 152 can have dimensions of about 7 mm by 14 mm; however, it should be appreciated that this size can vary.

Figure 1B:
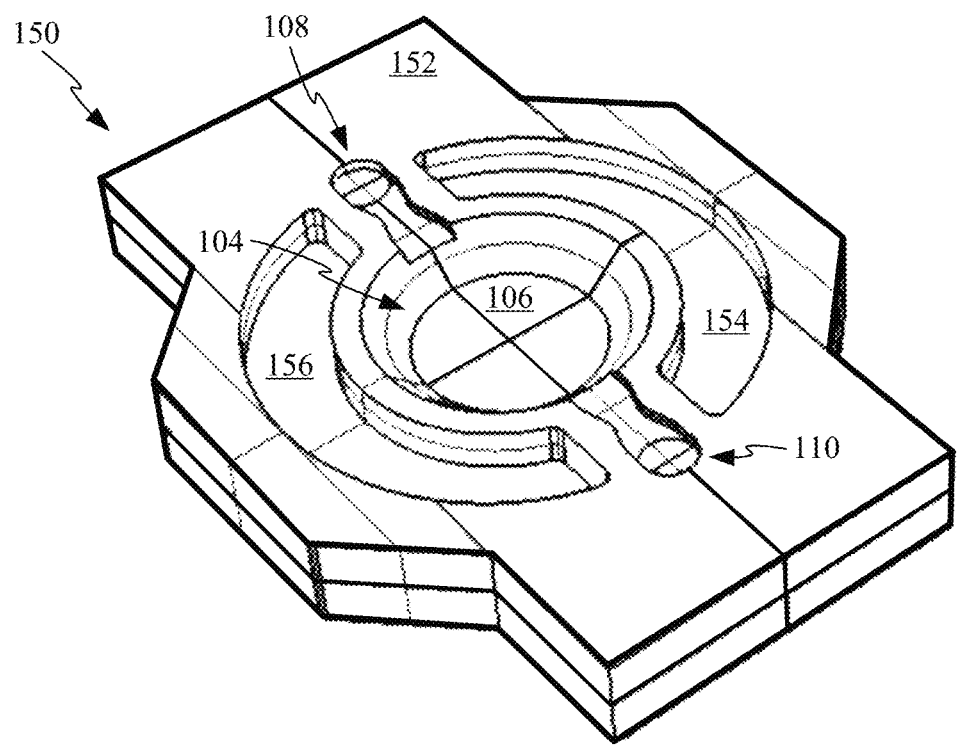
FIG. 1B shows another exemplary reaction vessel suitable for use with the described embodiments.

FIG. 1B shows a perspective view of another exemplary reaction vessel 150. Reaction vessel 150, similar to reaction vessel 100 includes housing component 152, reaction chamber 104, light absorbing layer 106, inlet channel 108 and outlet channel 110. Device housing 152 includes a widened central region that accommodates the inclusion of air gap regions 154 and 156. Air gap regions 154 and 156 can be left empty in order to discourage the lateral transmission of heat to adjacent reaction vessels. In some embodiments, the transfer of heat through air gap regions 154 and 156 can be further reduced by removing the air from air gap regions 154 and 156. In some embodiments, a diameter of housing component 152 can be about 5 mm; however, it should be appreciated that this size can vary. For example, the diameter of housing component 152 could vary from between 2 mm to 15 mm.

Figure 1C:
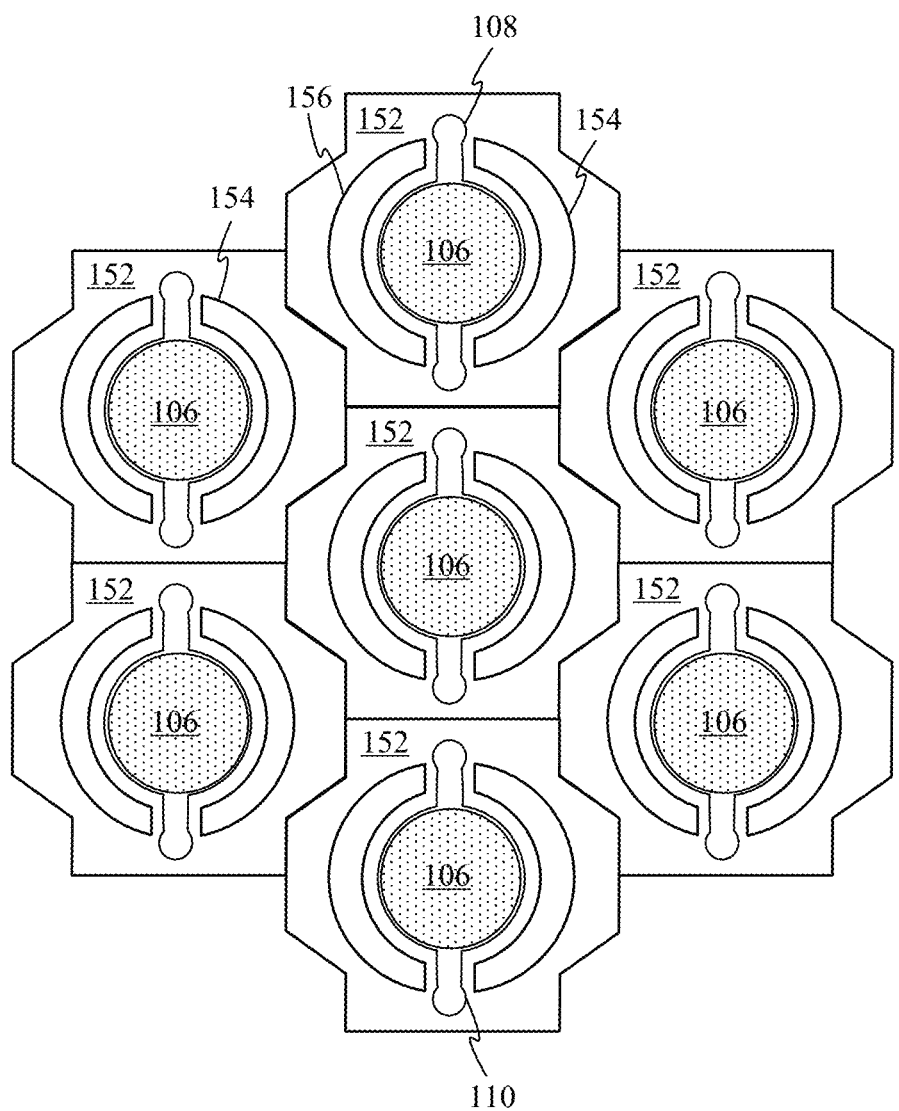
FIG. 1C shows how air gap regions establish robust barriers that reduce the lateral transfer of heat between adjacent reaction vessels.

FIG. 1C shows how the shape of housing component 152 allow reaction vessels 150 to be packed tightly into a honeycomb or hexagonal pattern. FIG. 1C also illustrates how air gap regions 154 and 156 are able to establish robust barriers that reduce the lateral transfer of heat between adjacent reaction vessels 150. When a diameter of reaction vessel 150 is about 5 mm reaction chamber 104 can hold about 10 µl of solution and have a depth of 800 µm. Generally, these devices are configured to hold between 2.5 µl and 500 µl with a depth of 200-1500 µm.

Figure 1D:
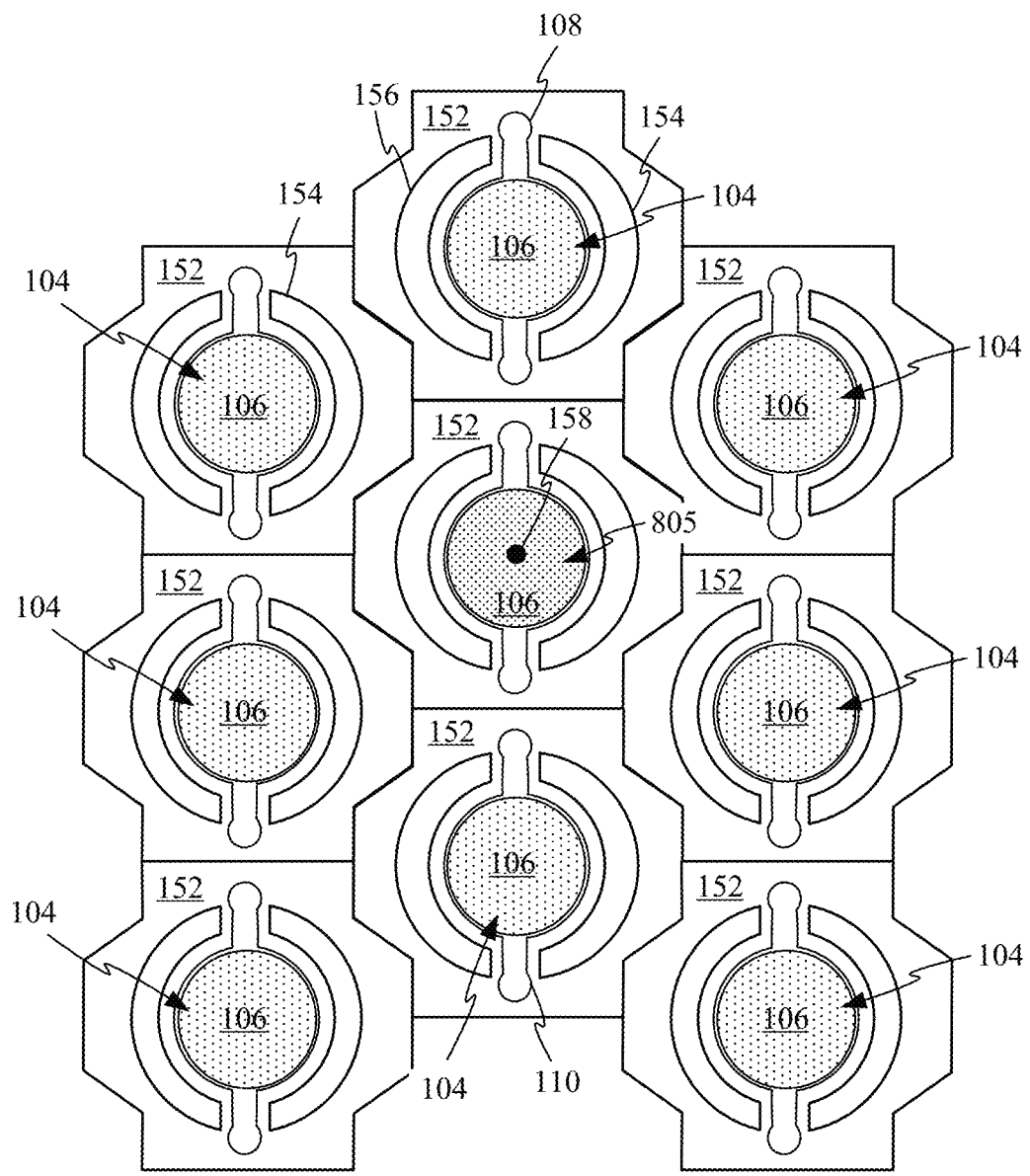
FIG. 1D shows housing components arranged in a hexagonal pattern with one of the housing components having a temperature sensor disposed within its reaction chamber.

FIG. 1D shows housing components 152 arranged in a hexagonal pattern with one of housing components 152 having a temperature sensor 158 disposed within chamber 805. Temperature sensor 158 may be incorporated within the chamber 805, and may be used to measure the heat introduced into chamber 805 by light absorbing layer 106 along with minimal amounts of laterally-flowing heat transfer from adjacent reaction chambers 104. A temperature measured by temperature sensor 158 within chamber 805 may be used to approximate a temperature of solution in nearby reaction chambers 104, as described in further detail below (e.g., in associated with FIGS. 8A-8F).

Figure 2A:
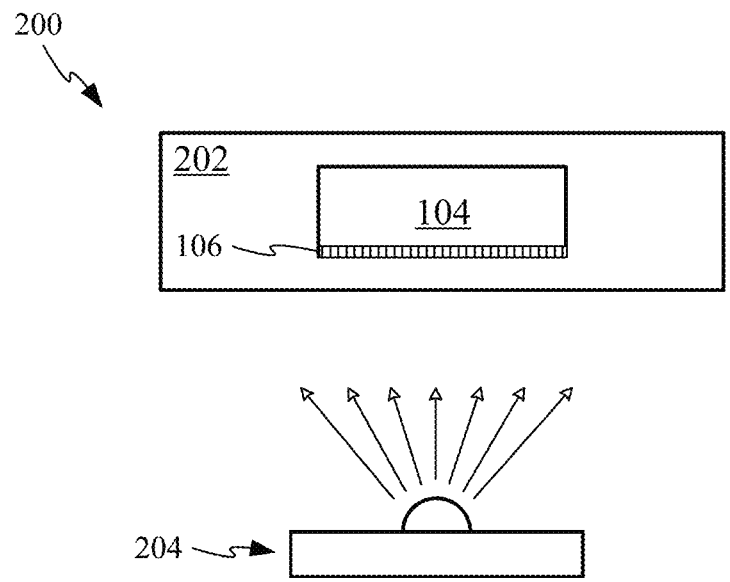
FIG. 2A shows a cross-sectional schematic view of an exemplary reaction vessel including a light absorbing layer that can take the form of a thin metallic film.

FIG. 2A shows a cross-sectional schematic view of an example reaction vessel 200. As illustrated, the reaction vessel 200 may include a reaction chamber 104 and a light absorbing layer 106 disposed within a housing 202. The light absorbing layer 106 may be disposed in a location that is adjacent to the reaction chamber 104. For example, the light absorbing layer 106 can take the form of a thin metallic film adhered to an interior-facing surface of housing 202 (e.g., light absorbing layer 106 may be formed on, deposited on, adhered to, or otherwise disposed on an interior-facing surface of the reaction chamber 104). As another example, the light absorbing layer 106 may be disposed adjacent to the reaction chamber 104, but may be covered with a substrate. In the example configuration shown in FIG. 2A, light absorbing layer 106 covers only one surface (e.g., a bottom surface) of reaction chamber 104. This configuration may allow for a large portion of the light emitted by energy source 204 to be absorbed by light absorbing layer 106. The energy from the photons making up the light are converted into heat energy, which is then thermally conducted into a solution within reaction chamber 104.

In some embodiments, heating the solution within reaction chamber 104 having a light absorbing layer 106 adjacent to only one interior-facing surface may generate a thermal gradient within reaction chamber 104 from a portion of the solution farthest from the light absorbing layer 106 to a portion of the solution that is proximate to the light absorbing layer 106. For example, a first portion of the solution farthest from light absorbing layer 106 may be heated more slowly than a second portion of the solution that is proximate to the light absorbing layer 106. In some embodiments, an operator may want to perform thermal cycles particularly quickly, in which case, DNA or other chemicals located within the first portion of the solution (e.g., farthest from light absorbing layer 106) may not be heated sufficiently quickly, and may thereby result in wasted material and/or lower yields. Alternatively or additionally, the second portion of the solution (e.g., proximate to the light absorbing layer 106) may be overheated, which may result in some amount of bleaching occurring to the materials within the solution, which can also negatively affect results of the operation. In part for this reason, in some embodiments it can be beneficial to illuminate opposing sides of the reaction vessel with two or more different energy sources (e.g., multiple LEDs, a single LED whose emitted energy is split into multiple parts to effectively create multiple sources from the point of view of the reaction vessel). This could be implemented by adding a second light absorbing layer to the opposite side of the reaction chamber. As will be further explained below, adding a second light absorbing layer increases uniformity of heating, increases the overall speed of heating, and increases the energy efficiency of heating.

Figure 2B:
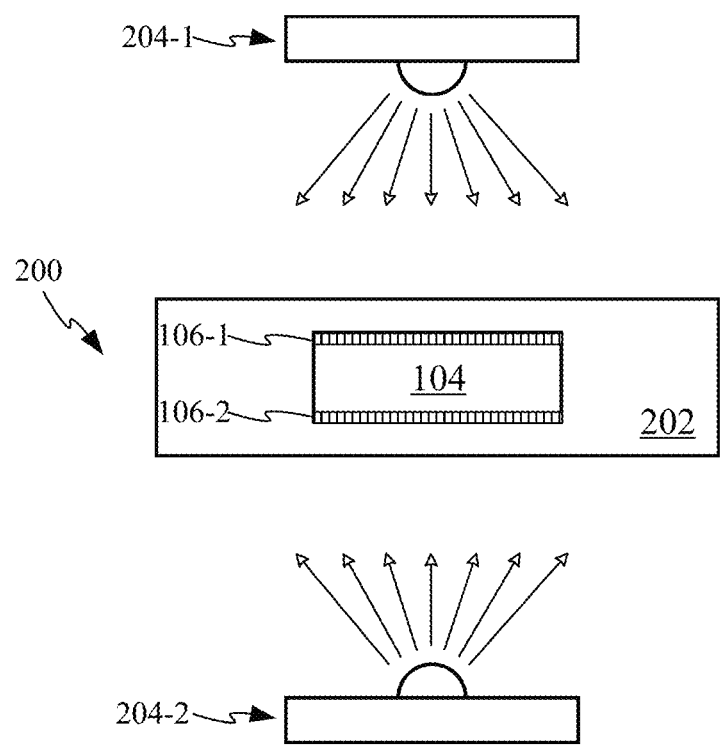
FIG. 2B shows how two light absorbing layers can be positioned upon or adjacent to opposing interior-facing surfaces of housing, which in part define reaction chamber.

FIG. 2B shows how two light absorbing layers 106-1 and 106-2 can be positioned upon or adjacent to opposing interior-facing surfaces of housing 202, which in part define reaction chamber 104. Light absorbing layers 106 can be configured to receive light from energy sources 204-1 and 204-2 (e.g., LEDs) positioned upon opposing sides of reaction vessel 200. Since this configuration allows heat to be introduced across a much larger area and on opposing sides of the reaction chamber, a solution within the reaction chamber 104 may experience a much smaller thermal gradient as compared to the example reaction chamber of FIG. 2A (which is heated from only one side). As a result, heating of the solution in the configuration illustrated in FIG. 2B may be more uniform than in the configuration illustrated in FIG. 2A. For this reason, over- or under-heating of the solution within reaction chamber 104 at any given point may be less likely. Additionally, heating the solution from multiple sides (e.g., from two opposing sides as shown in FIG. 2B) may result in faster heating of the solution, and as a result, may increase overall throughput for the reaction vessel. For example, a maximum rate at which the solution within reaction chamber 104 is thermally cycled can be increased when compared to the maximum rate achievable by illuminating only a single side of the configuration illustrated in FIG. 2A. This increase of the thermal cycling rate is at least in part a result of being able to double the surface area receiving photonic energy and the volume of heated film within reaction chamber 104. In some embodiments, at least a portion of other interior-facing surfaces can be covered in a light absorbing layer well suited for absorbing photonic energy. For example, the interior-facing surfaces of lateral walls defining reaction chamber 104 can be at least partially covered by a light absorbing layer. In some embodiments, additional energy sources 204 could be focused on these additional light absorbing layers to further increase the rate at which energy can be injected into reaction chamber 104. In some embodiments, the energy sources 204-1 and 204-2 may be adjustable such that they emit different energy levels or are otherwise adjustable (e.g., with one of the energy sources being closer to the reaction chamber 104 than the other) such that the light absorbing layers 106-1 and 106-2 receive different amounts of energy. In some embodiments, alternatively or additionally, the light absorbing layers 106-1 and 106-2 may be different (e.g., in composition, in dimensions such as thickness or surface area) such that they are configured to absorb different amounts of energy.

Figure 3A:
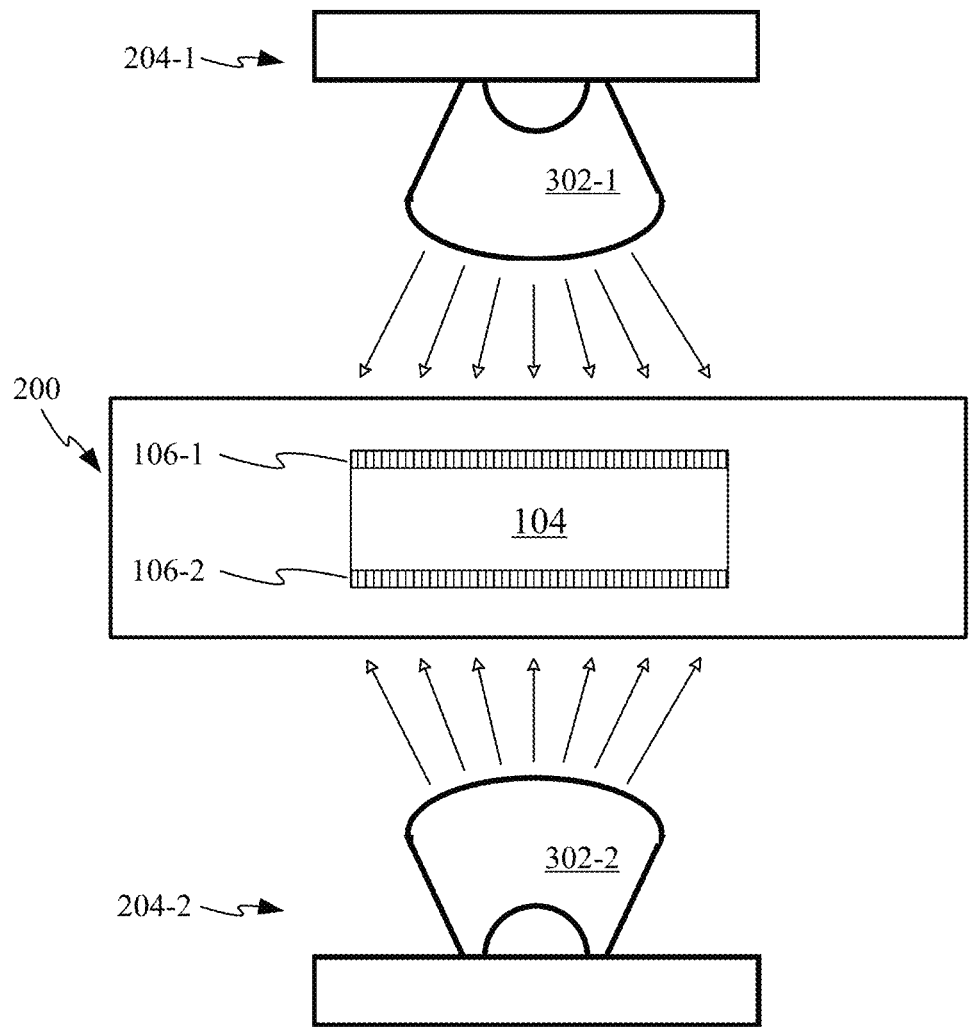
FIG. 3A shows an example configuration of light absorbing layers and can be positioned upon or adjacent to opposing interior-facing surfaces of housing with optical elements and that may be used to alter the characteristics of light generated by energy sources.

FIG. 3A shows an example configuration where light absorbing layers 106-1 and 106-2 can be positioned upon or adjacent to opposing interior-facing surfaces of housing 202, with optical elements 302-1 and 302-2 that may be used to alter the characteristics of light generated by energy sources 204-1 and 204-2. In some embodiments, these interior-facing surfaces of housing 202 may define reaction chamber 104 and the light absorbing layers 106 may be positioned upon (e.g., formed on, deposited on, adhered to, or otherwise disposed on) the interior-facing surfaces such that the lighted absorbing layers 106 may come into direct contact with a solution within reaction chamber 104. Alternatively, a substrate may be disposed over one or more of the light absorbing layers 106-1 and 106-2, such that they do not come into direct contact with the solution. FIG. 3A also shows how energy sources 204-1 and 204-2 can include one or more optical elements 302-1 and 302-2 configured to concentrate the light generated by energy sources 204-1 and 204-2 onto absorbing layers 106-1 and 106-2. Optical elements 302-1 and 302-2 can take the form of one or more lenses, light pipes, or baffles that at least partially collimate the light generated by energy sources 204-1 and 204-2. For example, optical elements 302-1 and 302-2 may include convex lenses that serve to focus the light generated by their respective energy sources. As another example, optical elements 302-1 and 302-2 may include baffles (e.g., with reflector elements) that are configured to focus the light generated by their respective energy sources. Optical elements 302-1 and 302-2 may help reduce the occurrence of waste light (e.g., by focusing light emitted by energy sources 204-1 and 204-2 such that almost all the light is incident on the light absorbing layers 106-1 and 106-2) and maximize the amount of power available to add into a solution within reaction chamber 104. In some embodiments, other optical elements can be used to help guide uniform light from energy sources 204-1 and 204-2 toward reaction chamber 104. For example, a light pipe could be used to transport light from energy sources 204-1 and 204-2 directly to various locations on reaction chamber 104. The light pipe could be advantageously shaped to deliver larger amounts of light to specific regions of light absorbing layers 106-1 and 106-2. In some embodiments, the light pipe could extend at least partially within housing 202. In some embodiments, as described above, the energy sources 204-1 and 204-2 may be adjustable, the light absorbing layers 106-1 and 106-2 may be different, and/or the optical elements 302-1 and 302-2 may be different, such that absorption of light by the light absorbing layers 106-1 and 106-2 may be fine-tuned.

Figure 3B:
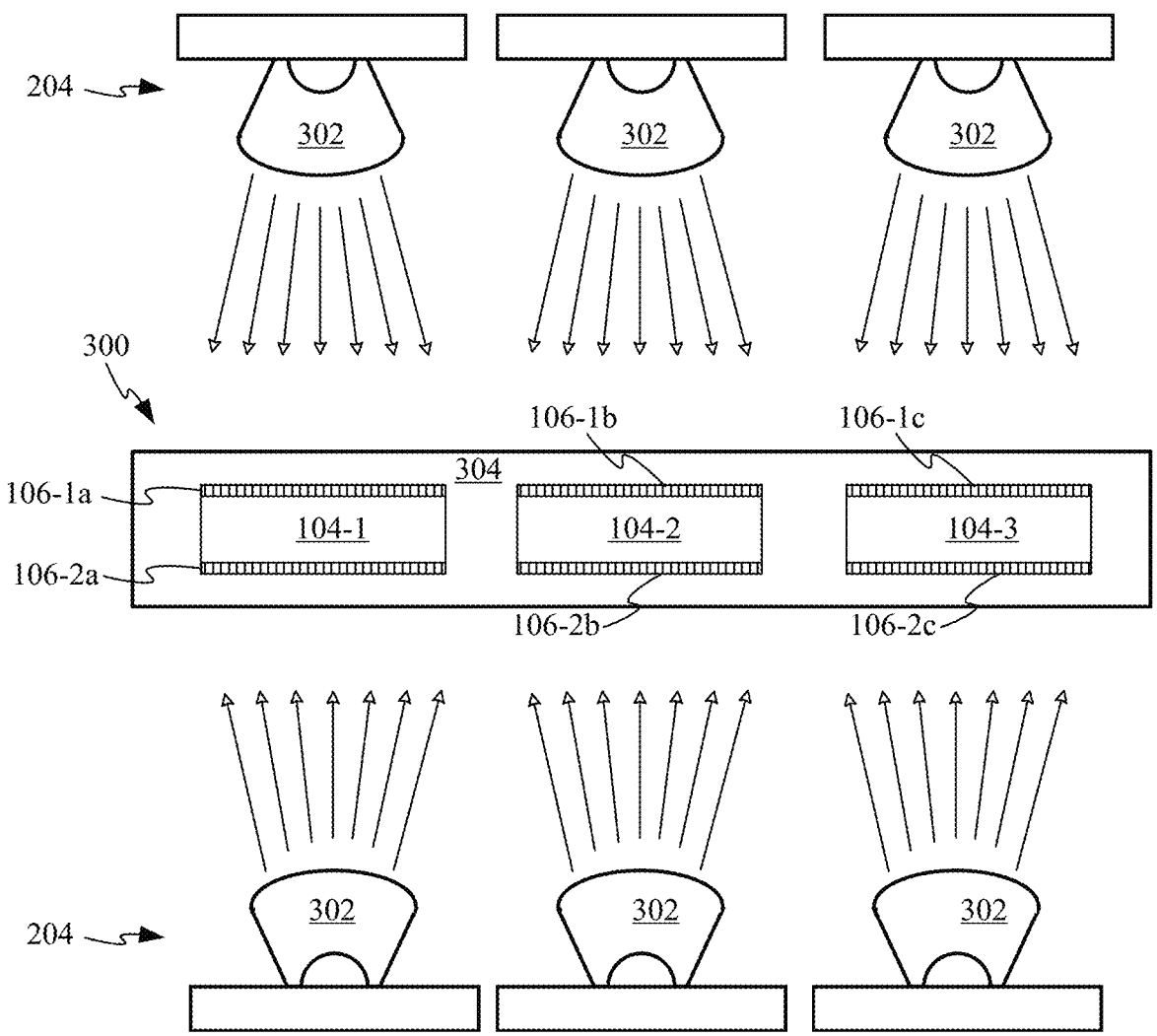
FIG. 3B shows how multiple reaction chambers can be positioned within a housing of a reaction vessel.

FIG. 3B shows how multiple reaction chambers 104-1, 104-2, and 104-3 can be positioned within a housing 304 of a reaction vessel 300. In some embodiments, solution can be transferred between adjacent reaction chambers 104-1, 104-2, and 104-3 by internal channels that can be defined by housing 304. In this way, one stream of solution can traverse multiple reaction chambers 104-1, 104-2, and 104-3. Alternatively, the reaction chambers 104-1, 104-2, and 104-3 may not be separated by physical barriers, and as such may not require channels. For example, the reaction chambers 104-1, 104-2, and 104-3 illustrated in FIG. 3B may be disposed within a single chamber of the reaction vessel 300 with no partitions in between. In some embodiments, as illustrated in FIG. 3B, the reaction chambers may have light absorbing layers made up of several discrete regions (e.g., 106-1*a*, 106-1*b*, and 106-1*c*, 106-2*a*, 106-2*b*, and 106-2*c*). In some embodiments, these discrete regions may be separated from each other. In some embodiments, any of these discrete regions may have different characteristics, such that they have different temperature profiles. For example, discrete regions 106-1*a* and 106-2*a* could have a different thickness and/or composition than discrete regions 106-1*b* and 106-2*b*, allowing for energy to be absorbed more quickly into a solution within the reaction chamber 104-1 as compared to the reaction chamber 104-2. Alternatively or additionally, energy absorption among different reaction chambers 104 may be varied by adjusting the power levels of the energy sources 302. Varying energy absorption among reaction chambers 104-1, 104-2, and 104-3 may be beneficial where multi-step reactions, one or more of which require different temperatures, are necessary. For example, a single PCR cycle has multiple steps that require different temperatures (e.g., for denaturing DNA, annealing, and extending).

In some embodiments, temperatures within reaction chambers 104-1, 104-2, and 104-3 may be varied by assigning multiple energy sources to each reaction chamber 104. This may be particularly advantageous in cases where energy sources 204 may only have ON and OFF states. For example, three energy sources 204 may be assigned to a single reaction chamber 104-1. One or more of these energy sources 204 may be turned ON, and the number of energy sources 204 that are ON would determine the amount of energy delivered to the reaction chamber 104-1. By turning ON and OFF individual energy sources 204, the temperature within the reaction chamber 104 may be varied along a scale. In this example, turning ON all 3 energy sources 204 may result in the highest temperature value, turning on two of the energy sources 204 may result in an intermediate temperature value, and turning on one of the energy sources 204 may result in a low temperature value. In some embodiments, as illustrated in FIG. 3B, the effects of energy sources 204 may not be limited to a single reaction chamber (e.g., the reaction chamber 104-1). For example, the left-most energy source illustrated in FIG. 3B may deliver energy to both 104-1 and 104-2. As such, energy received by any one of the chambers 104-1, 104-2, and 104-3 may be varied (e.g., across a gradient) by turning ON or OFF the illustrated energy sources 204. In some embodiments, energy sources 204 could also be equipped with controllers that allow for a variety of duty cycles to be applied that effectively allow the amount of light emitted by each of energy sources 204 to vary greatly. For example, a pulsed control signal could be provided to one of energy sources 204 that results in that energy source 204 only transmitting light 50% of the time, thereby effectively halving the amount of light transmitted to a light absorbing layer as compared to a different energy source 204 that transmits light 100% of the time.

Figure 4:
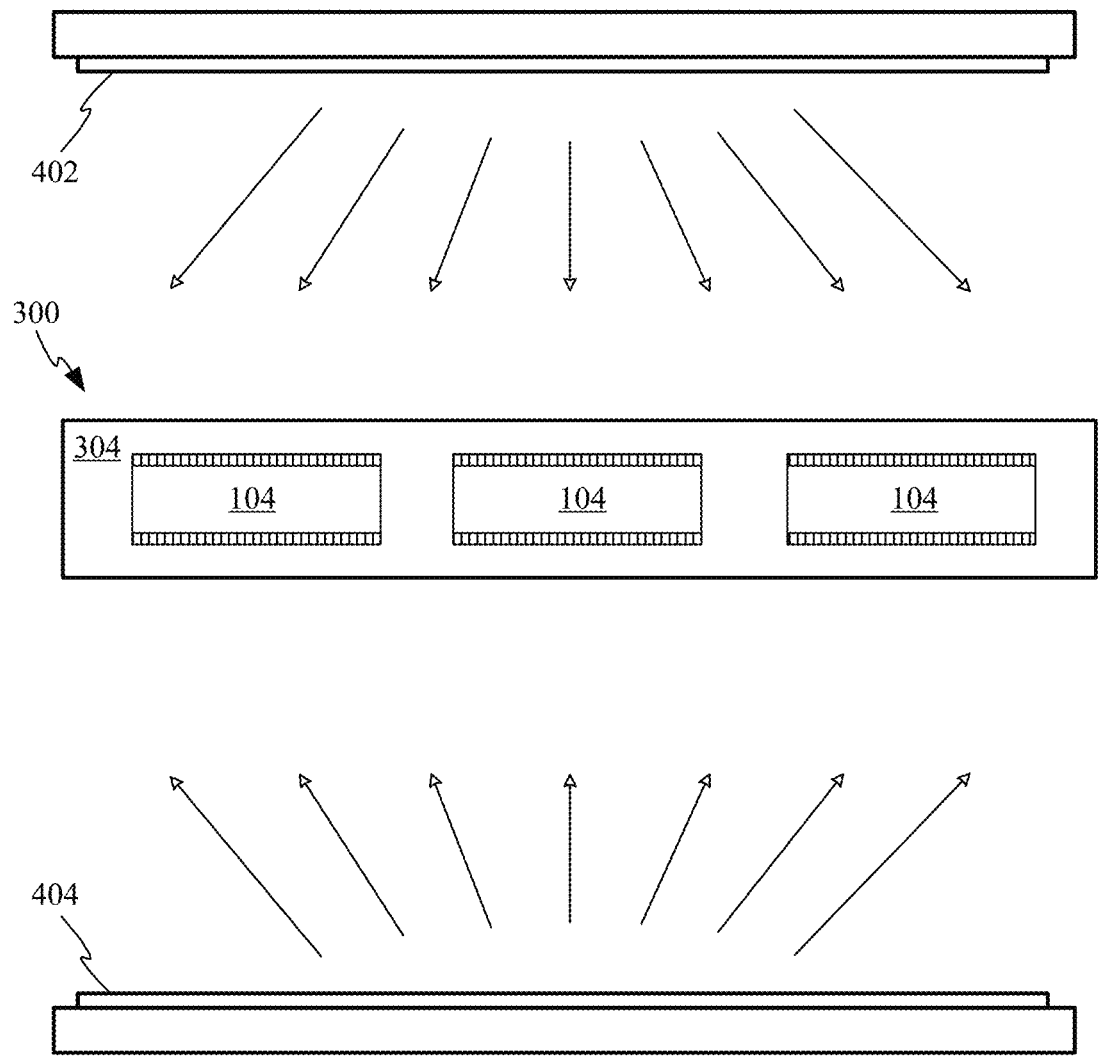
FIG. 4 shows an example embodiment in which an energy source takes the form of a chip on board (COB) LED that may be well suited for distributing light evenly across a relatively large area of housing of reaction vessel.

FIG. 4 shows an example embodiment in which an energy source takes the form of a chip on board (COB) LED 402 that may be well suited for distributing light evenly across a relatively large area of housing 304 of reaction vessel 300. In some embodiments, COB LED 402 can be constructed from multiple LED chips that are surface mounted to a printed circuit board (PCB). In these embodiments, each of the LED chips (or subsets thereof) may be individually controlled such that an amount of light energy outputted and/or a direction at which the light energy is outputted may be controlled (similar to FIG. 3B). One advantage of the COB LED is that reaction chambers 104 can be separated by any interval or pattern without the need for rearranging individual energy sources. This type of configuration also reduces the need for optical elements that target specific reaction chambers 104. In some embodiments, however, COB LEDs 402 and 404 could include baffles or optical elements that are configured to prevent the light emitted from COB LEDs 402 and 404 from being diverted to either side of housing 304.

Figure 5A:
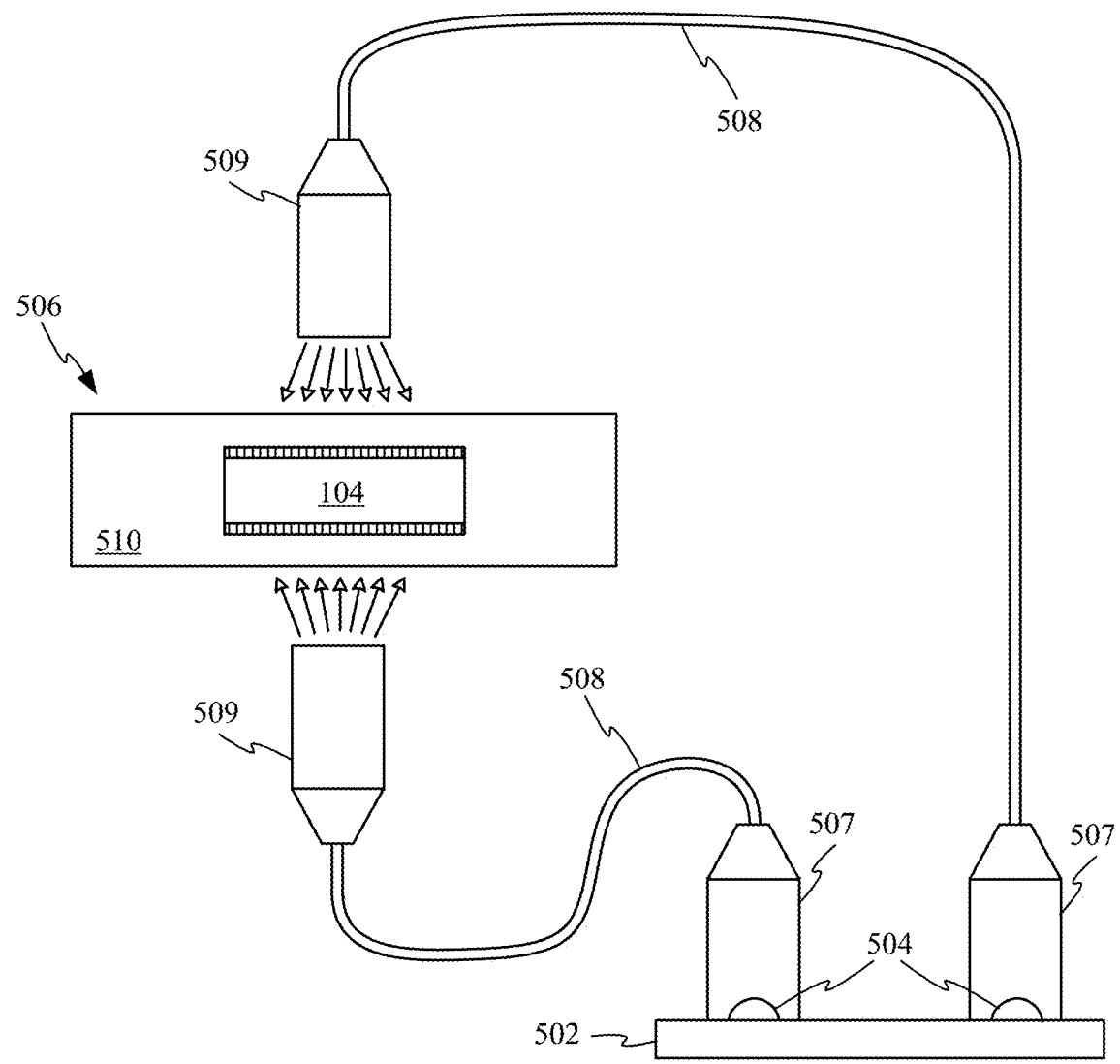
FIG. 5A shows an example embodiment with a PCB supporting multiple LEDs that can be used to illuminate opposing sides of a reaction chamber of reaction vessel.

FIG. 5A shows an example embodiment with a PCB 502 supporting multiple LEDs 504 that can be used to illuminate opposing sides of a reaction chamber 104 of reaction vessel 506. The light emitted by LEDs 504 can be transmitted by optical fibers 508, which are able to receive and transmit that light with little or no loss to a point just above an exterior surface of housing 510 of reaction vessel 506. Optical fibers 508 may include receiving ends 507 and transmitting ends 509 that are configured to efficiently gather and transmit light, respectively. Although FIG. 5A illustrates a PCB supporting two LEDs that illuminate opposing sides of a reaction chamber, the disclosure contemplates a PCB supporting any number of LEDs that illuminate any number of suitable regions of a reaction vessel.

Figure 5B:
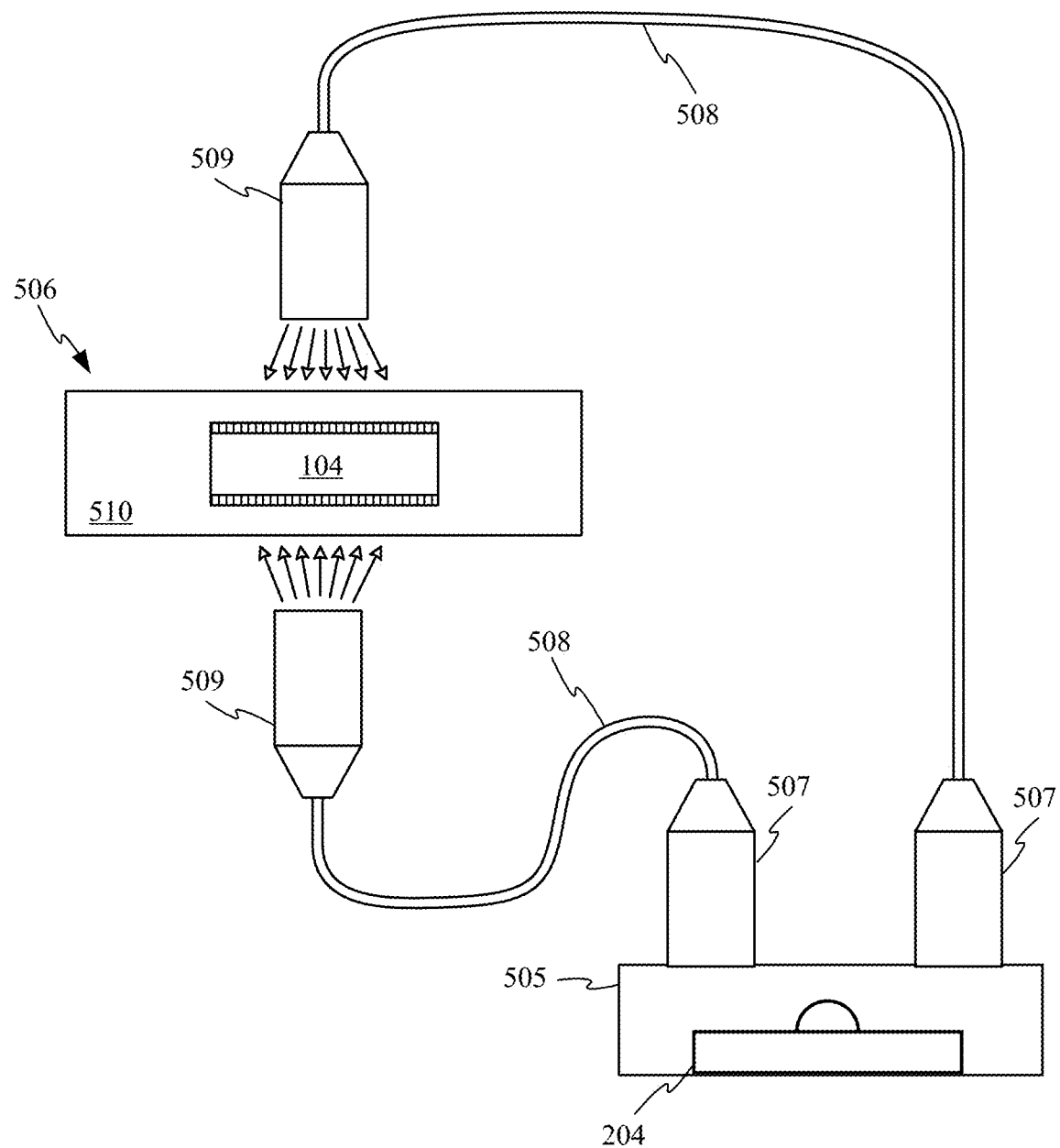
FIG. 5B shows an example embodiment where light energy from a single precursor energy source (e.g., the LED) is split between two optical fibers to illuminate opposing sides of a reaction chamber of reaction vessel.

FIG. 5B shows an example embodiment where light energy from a single precursor energy source (e.g., the LED 204) is split between two optical fibers 508 to illuminate opposing sides of reaction chamber 104 of reaction vessel 506. In the illustrated example, the LED 204 is housed within an LED housing 505 to which receiving ends 507 of the optical fibers 508 are coupled. The LED housing 505 may be optimized with optical elements and/or reflectors (e.g., disposed along its interior-facing surfaces) for maximizing efficiency of light transmission. Although FIG. 5B illustrates splitting light energy from a one LED between two optical fibers to illuminate opposing sides of a reaction chamber, the disclosure contemplates splitting light energy from any number of LEDs among any number of optical fibers to illuminate any number of suitable regions of a reaction vessel.

Figure 5C:
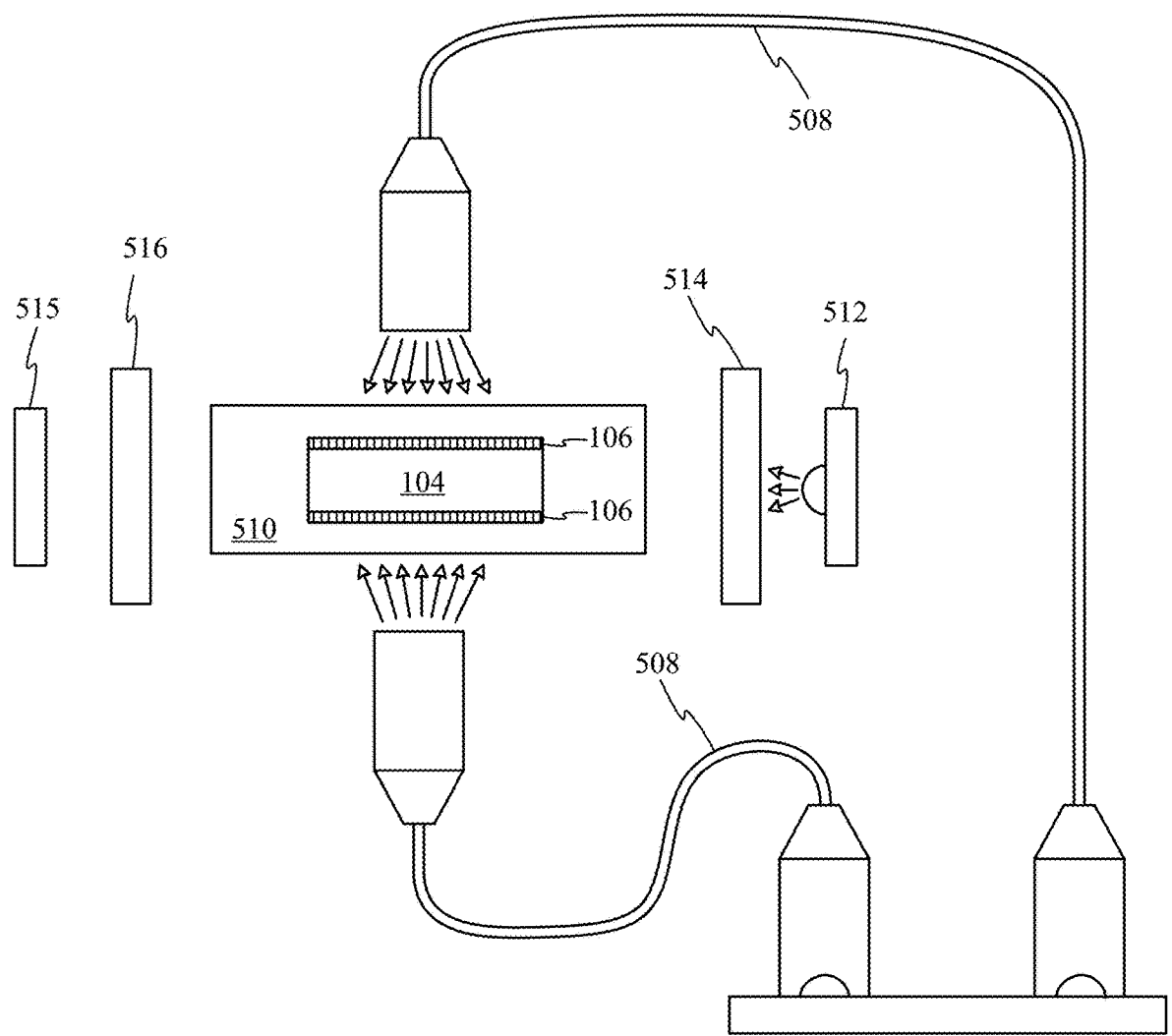
FIG. 5C shows the energy source configuration depicted in FIG. 5A with the addition of an excitation light source assembly and an emission detecting sensor assembly.

FIG. 5C shows the energy source configuration depicted in FIG. 5A with the addition of an excitation light source assembly and an emission detecting sensor assembly. In some embodiments, the excitation light source assembly can include excitation LED 512. In some embodiments, excitation LED 512 can be configured to emit visible-spectrum light that is able to cause any fluorescent markers present within reaction chamber 104 (e.g., fluorescent markers bound to DNA strands or nucleotides) to emit fluorescent light. In some embodiments, an excitation filter 514 may optionally be used to remove any wavelengths of light generated by excitation LED 512 that are outside of a wavelength range that excites the fluorescent markers. In some embodiments, a wavelength range of excitation filter 514 can be adjusted to match fluorescent markers being used for a particular experiment or reaction. In some embodiments, the emission detecting sensor assembly can include emission detecting sensor 515 configured to detect a fluorescent light emitted by fluorescent markers within the reaction chamber in response to light from the excitation LED 512. In some embodiments, an emission filter 516 may optionally be used to optimize (e.g., amplify, filter) light that is transmitted to the emission detecting sensor 515. In some embodiments, emission detecting sensor 515 can take the form of a photodiode, CMOS or CCD sensor capable of receiving emissions from the fluorescent markers within reaction chamber 510. In some of these embodiments, the photodiode, CMOS or CCD sensors can be calibrated so that in addition to recognizing the presence of the fluorescent markers, a position of the fluorescent markers within reaction chamber 104 can also be determined. It should be noted that while the emission detecting sensor assembly is depicted as being on an opposite side of reaction chamber 104 from the excitation light source assembly that in some embodiments, the two assemblies can be positioned in any suitable location with respect to each other (e.g., on the same side of reaction chamber 104). For example, the excitation light source assembly could be positioned on the same side, but offset laterally by about 30 degrees. In some embodiments, the emission filter 516 (which may allow only certain wavelengths to pass through) may serve to block or filter out light emitted by the optical fibers 508 such that the light emitted by the optical fibers 508 does not intermix with the light from the excitation assembly (e.g., the excitation LED 512) so that sensor readings of the emission detecting sensor 515 are based on fluorescent light and not compromised by light from the optical fibers 508. For example, the emission filter may be configured to allow light of one or more wavelengths corresponding to the florescent light, and block or filter out light of one or more other wavelengths (e.g., thereby filtering out or at least significantly reducing light from the optical fibers 508). Additionally, at least in some embodiments, all or most of the light from the optical fibers 508 used to illuminate light absorbing layers 106 may generally be prevented from entering into reaction chamber 104 by the light absorbing layers 106. As such, intermixing may not be as much of an issue in these embodiments. In some embodiments, a system associated with the reaction vessel may log (e.g., within a memory) one or more of an indication that a threshold amount of fluorescent light was detected (e.g., an amount above background artifact signals from a fluorescent dye), a value quantifying the amount of emitted fluorescent light, a position within a reaction vessel or chamber at which the fluorescent light was detected, a time point at which the florescent light was detected, and a temperature of the associated reaction chamber at the time point at which the florescent light was detected. In these embodiments, the logged data can be used to synthesize information about a reaction, assay, or experiment. For example, a graph illustrating a temperature and fluorescence profile during an assay or reaction (e.g., PCR) may be mapped for analysis.

Figures 6A, 6B:
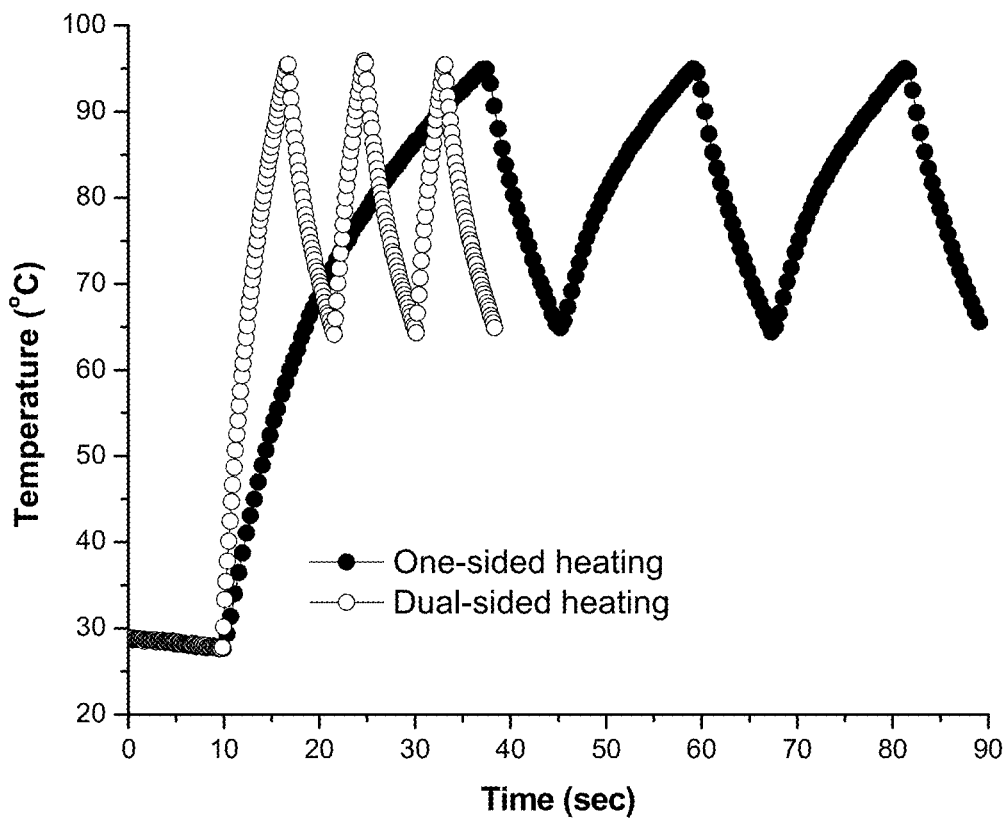
FIGS. 6A-6B show experimental data from three consecutive heating and cooling test cycles comparing temperature profiles of a reaction chamber being heated from one side (one-sided heating) and a reaction chamber being heated from two sides (dual-sided heating)

FIGS. 6A-6B shows experimental data from three consecutive heating and cooling test cycles comparing temperature profiles of a reaction chamber being heated from one side (one-sided heating) and a reaction chamber being heated from two sides (dual-sided heating). Contrary to early predictions, dual-sided heating does not simply result in a reaction chamber being heated at twice the speed as one-sided heating. In fact, unpredictably, the ramp-up times with dual-sided heating occur at much more than twice the speed of ramp-up times with one-sided heating. For example, as illustrated in the graph of FIG. 6A and the corresponding table of FIG. 6B, it took 6.81 seconds for the reaction chamber to be heated from room temperature to about 95° C. (i.e., the first test cycle) using dual-sided heating, while it took 27.43 seconds for the same temperature increase using one-sided heating. As such, double-sided heating in this cycle was about four times faster than one-sided heating. Similarly, ramp-up times in the second and third test cycles were more than four times faster in the case of double-sided heating, as shown in FIGS. 6A-6B. Even more unpredictably, the cool-down times (e.g., during which energy was not transmitted to light absorbing layers of the reaction chamber to cause a temperature decrease in the reaction chamber) was also affected. For example, referring to the first test cycle in FIGS. 6A-6B, it took 4.71 seconds for the reaction chamber to ramp down from about 95° C. to about 65° C. in a reaction chamber that was heated up using double-sided heating, while it took 7.47 seconds for the same temperature decrease in a reaction chamber that was heated up using one-sided heating. As such, cooling a reaction chamber heated with double-sided heating was about 1.6 times faster in this cycle. Cool-down times in the other cycles were similarly faster with a reaction chamber that was heated with double-sided heating. These unpredictable results are at least in part due to the fact that, with dual-sided heating, less heat is dissipated from the light absorbing layers of reaction chambers to the housing surrounding the reaction chamber while getting the reaction chamber up to a desired temperature. For example, heating from both sides heats the reaction chamber more quickly from the beginning. The effects of this quicker heating compounds synergistically over a heating period, because less time spent heating translates to less loss of heat to the housing around the reaction chamber (in one-sided heating, the additional heat loss would need to be compensated for during the heating period to achieve a desired temperature in the reaction chamber). In addition, introducing heat from opposing sides acts to confine heat within the reaction chamber, thereby again reducing loss of heat. For example, in one-sided heating, a first side opposite a light absorbing layer disposed on a second (heated) side may allow for a temperature gradient that facilitates heat from the reaction chamber to escape via the first side. By contrast, such a gradient would not exist in dual-sided heating, thereby trapping heat within the chamber, and thereby speeding up heating. As for the quicker cool-down times, this too is at least in part due to the reduced loss of heat in dual-sided heating. For example, since less heat is absorbed by the surrounding housing during dual-sided heating, when energy is no longer transmitted to let absorbing layers of the reaction chamber, more heat can be dissipated away from the reaction chamber to the housing surrounding the reaction chamber. By contrast, in single-sided heating, since the housing already has a relatively higher temperature due to more heat dissipation, the temperature gradient between the reaction chamber and the surrounding housing is much smaller. This may result in slower heat transfer away from the reaction chamber, resulting in slower cool-down times.

FIG. 7 illustrates an example method 700 for operating a temperature-controlled reaction vessel system. The method may begin at step 710, where a reagent is introduced into a first reaction chamber, wherein the first reaction chamber comprises a first light absorbing layer and a second light absorbing layer, the first and second light absorbing layers having an inner surface that is oriented toward an interior of the first reaction chamber and an outer surface that is oriented away from the interior of the first reaction chamber. At step 720, a first energy source may direct a first light toward the outer surface of the first light absorbing layer so as to heat the first light absorbing layer. At step 730, a second energy source may direct a second light toward the outer surface of the second light absorbing layer so as to heat the second light absorbing layer. At step 740, heat from the first and second light absorbing layers may be transferred to the reagent.

Particular embodiments may repeat one or more steps of the method of FIG. 7, where appropriate. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates an example method for operating a temperature-controlled reaction vessel system, including the particular steps of the method of FIG. 7, this disclosure contemplates any suitable method for operating a temperature-controlled reaction vessel system, including any suitable steps, which may include all, some, or none of the steps of the method of FIG. 7, where appropriate. Furthermore, although this disclosure describes and illustrates particular components, devices, or systems carrying out particular steps of the method of FIG. 7, this disclosure contemplates any suitable combination of any suitable components, devices, or systems carrying out any suitable steps of the method of FIG. 7.

Figure 8A:
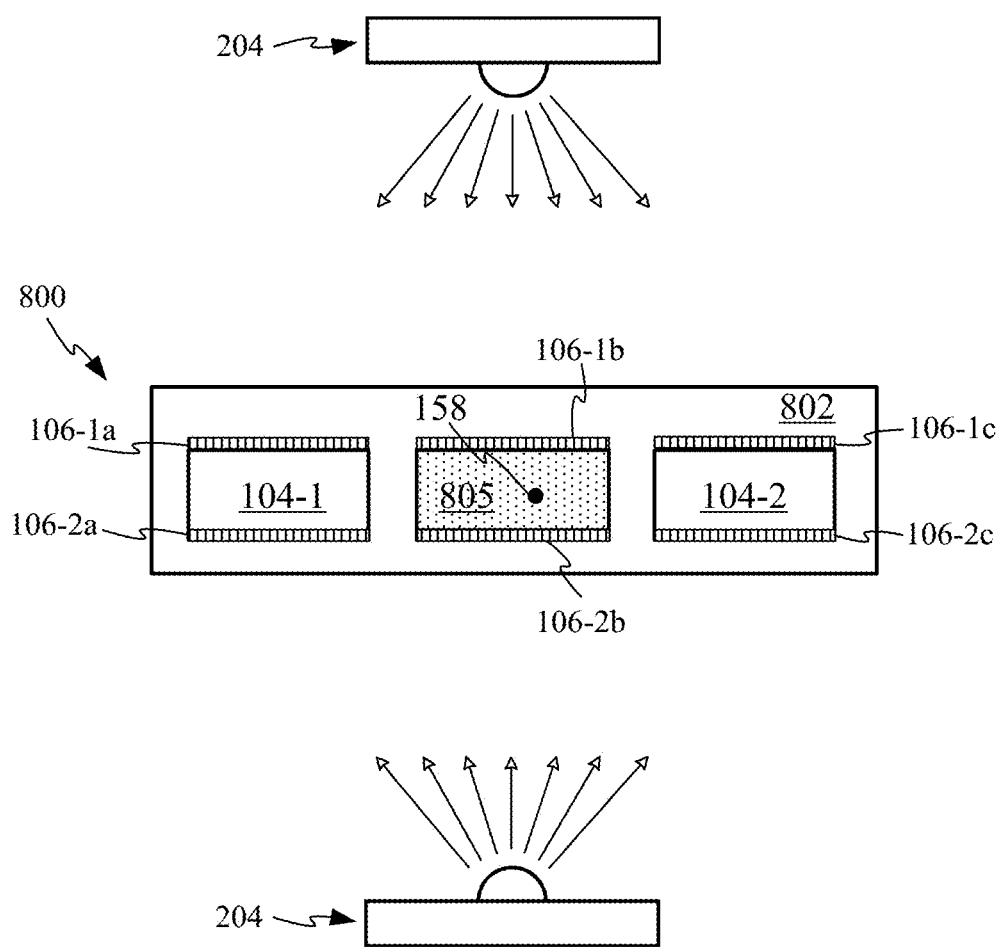
FIG. 8A shows an example reaction vessel with a housing that defines multiple reaction chambers that can be filled with solution and a chamber that includes a temperature sensor.

FIG. 8A shows an example reaction vessel 800 with a housing 802 that defines multiple reaction chambers 104 that can be filled with solution and a chamber 805 that includes a temperature sensor 158. In some embodiments, a solution (e.g., one containing nucleotides or reagents) can be introduced into reaction chambers 104-1 and 104-2 of reaction vessel 800. As illustrated, reaction vessel 800 may also include chamber 805, which includes temperature sensor 158. In some embodiments, the chamber 805 may be filled with a viscous fluid (e.g., a liquid polymer). The viscous fluid may help keep temperature sensor 158 in a fixed position within reaction chamber 805. In some embodiments, the viscous fluid can take the form of a liquid polymer or adhesive that can be cured (and solidified) to further prevent movement of temperature sensor 158 within chamber 805. Similar to the reaction chambers 104, the chamber 805 may be associated with one or more light absorbing layers that are configured to heat the chamber 805 along with the reaction chambers 104. For example, as illustrated in FIG. 8A, the reaction vessel 800 may have a first light absorbing layer that includes discrete regions 106-1a, 106-1b, and 106-1c and a second light absorbing layer that includes discrete regions 106-2a, 106-2b, and 106-2c. In this example, the discrete regions 106-1a, 106-1c, 106-2a, and 106-2c are associated with reaction chambers 104-1 and 104-2, and the discrete regions 106-1b and 106-2b are associated with the chamber 805. In some embodiments, temperature sensor 158 may be placed within a central region of reaction chamber 805 that allows it to gather an average temperature of the chamber 805. It should be noted that in some embodiments the average temperature may not be at the absolute center of reaction chamber 805 and this position may be shifted (e.g., closer to or farther away from the light absorbing layer) to achieve desired temperature sensor readings. In some embodiments, each of reaction chambers 104-1, 104-2 and 805 may be similarly sized and may receive about the same amount of light from energy source 204. As such, each may receive about the same amount of photonic energy and in some instances results in a temperature within reaction chambers 104-1, 104-2 and 805 being substantially the same. This allows for accurate measurement of temperature within multiple reaction chambers using only a single temperature sensor 158. Having a temperature sensor within a chamber may be particularly advantageous in some cases, particularly where heat transfer rate is extremely quick (as may be the case with the heating mechanisms involving light absorbing layers as described herein). Conventional temperature monitoring systems, which place temperature sensors outside the reaction vessel (e.g., within a platform system onto which the reaction vessel is mounted), are typically not effective with such quick-heating mechanisms and can create issues with over- or under-heating, due to inaccurate real-time measurements. For example, such systems may include too much material and/or multiple layers (e.g., of the housing of the reaction vessel and/or of the platform system) for efficient heat transfer between the reaction chamber and the temperature sensor. As such, there may be a delay in detecting temperature changes accurately. While this delay may be tolerable in cases where reaction chambers are heated relatively slowly, it can be impermissible in cases where heating occurs rapidly. By placing temperature sensors within a chamber so as to approximate conditions within reaction chambers, real-time measurements may be accurate.

Figure 8B:
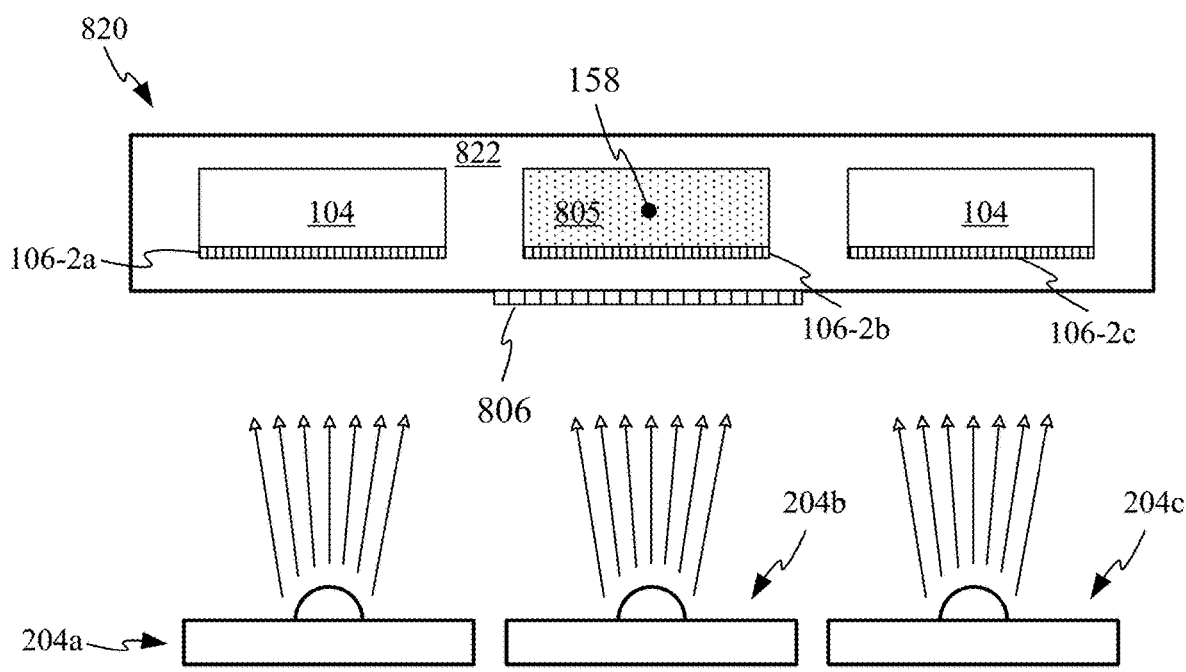
FIG. 8B shows a reaction vessel that includes a housing defining at least two reaction chambers, a chamber that includes a temperature sensor, and a light diffusing layer.

FIG. 8B shows a reaction vessel 820 that includes a housing 822 defining at least two reaction chambers 104, a chamber 805 that includes a temperature sensor 158, and a light diffusing layer 806. The temperature sensor 158 may be capable of measuring an internal temperature within the chamber 805. In some embodiments, the reaction chambers 104 and the chamber 805 may be configured to have the same dimensions (e.g., the same size and shape) and may have the discrete regions 106-2a, 106-2b, and 106-2c that are substantially the same. In other embodiments, any of these characteristics may be varied. In some embodiments, the contents of reaction chambers 104 may be different than the chamber 805. As described elsewhere, the chamber 805 can be filled with a potting material (e.g., a viscous fluid or a cured polymeric material) that may be configured to pre-fill the chamber 805 such that it prevents or reduces movement of sensor 158 within the chamber 805. For example, the chamber 805 may be filled with a polymeric material such as a silane-modified polymer or liquid adhesive that can be converted to a solid by undergoing a thermal- or UV-curing operation.

Filling the chamber 805 with a potting material offers the ability to fix the temperature sensor 158 in place within reaction chamber 104 and transfer heat from light absorbing material to temperature sensor, so that temperature measurements are more precise. Using a potting material rather than a water-based solution that may more closely mimic the solution in reaction chambers 104 has the added advantage of affording convenient reusability. For example, in some embodiments, the reaction vessel 820 may be configured to be reused over the course of a large number of different operations. In these embodiments, the chamber 805 may be filled with a potting material (e.g., a polymeric material) that has material properties allowing it to withstand a large number of thermal cycles. If the chamber 805 were filled with, for example, water or a water-based solution, the water or water-based solution may evaporate over time (e.g., especially considering that many reactions within the reaction vessel may be conducted at high temperatures) such that temperature readings would not be precise over time. Moreover, the chamber 805 cannot be filled with air, because air is not a medium that allows for efficient heat transfer and therefore does not allow for accurate temperature measurements. As such, a potting material such as a polymeric material is particularly effective.

While the potting material can also be chosen to match a thermal conductivity and specific heat of the solution in the other reaction chambers 104, in some cases, an exact match may not be possible. For example, a specific heat of a polymeric material in chamber 805 can be substantially lower than the contents of reaction chambers 104 (e.g., a water-based PCR solution with DNA, polymerase enzyme), such that the temperature profile of the chamber 805 may be different from the temperature profile of the reaction chambers 104. As a result, in this example, the polymeric material in chamber 805 may heat more quickly than the water-based solution in the other reaction chambers 104, even though the light sources 204a, 204b, and 204c may be directing the same amount of energy toward the reaction chambers 104 and the chamber 805. As such, in this example, the temperature value detected by the temperature sensor 158 may not be an accurate representation of the temperature within the reaction chambers 104. To rectify this difference in the rate of heating, a light diffusing layer 806 can be added to the reaction vessel in between energy sources and the chamber 805. For example, as illustrated in FIG. 8B, the light diffusing layer 806 may be disposed along a surface of housing 822, such that light energy from the energy sources (e.g., the energy source 204b) must travel through the light diffusing layer 806 before it hits the discrete region 106-2b. In some embodiments, a light diffusing layer may be a material that is configured to reflect or scatter a portion of the light that is incident to the light diffusing layer. In some embodiments, light diffusing layer 806 can be specifically tuned to reduce the amount of light incident to light absorbing layer 106-2b by an amount calculated to account for a difference between the specific heat of the potting material in the chamber 805 and the (e.g., water-based) solution within the other reaction vessels 104. This configuration reduces the amount of light received at the light absorbing layer 106-2b, which can help compensate for the lower specific heat of the potting material in the chamber 805. In some other embodiments, a light blocking layer may be used in place of a light diffusing layer. For example, a light blocking layer may include one or more opaque sections that prevent segments of light transmitted by an energy source from passing through toward the chamber 805. In other embodiments, a filter layer may be employed to filter out certain wavelengths of light, such that the light that passes the filter layer is of reduced energy. In a configuration such as the one shown in FIG. 8B, an output of the energy source 204b directed at discrete region 106-2b can also be reduced to help compensate for the thermal characteristics of the potting material within the chamber 805. Although this disclosure focuses on a potting material within chamber 805 that has a lower specific heat than the contents of reaction chambers 104, this disclosure also contemplates embodiments with a potting material within chamber 805 that has a higher specific heat than the contents of reaction chambers 104. In these embodiments, the reaction vessel may be varied to increase absorption of heat energy of chamber 805 so as to compensate for the difference.

Figure 8C:
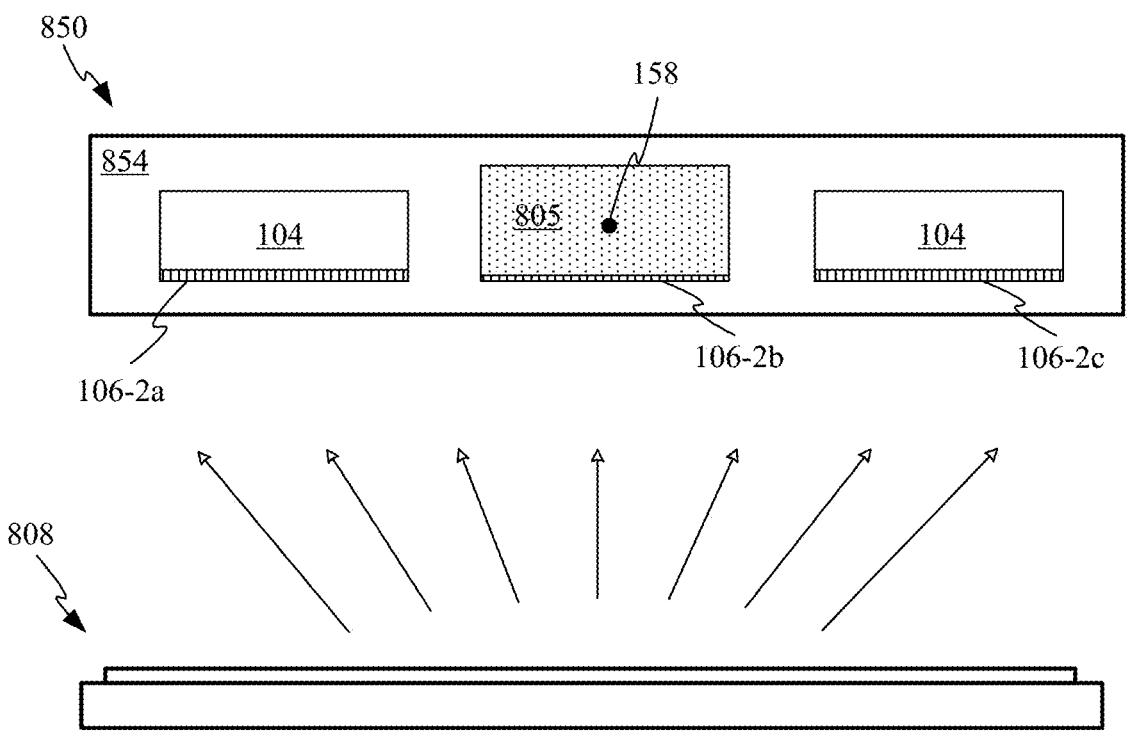
FIG. 8C shows a reaction vessel having a housing defining a chamber that is different from the reaction chambers.

FIG. 8C shows a reaction vessel 850 having a housing 854 defining a chamber 805 that is different from the reaction chambers 104. As illustrated, chamber 805 includes a temperature sensor 158 that is surrounded and fixed in place (e.g., by a solidified polymeric material). The reaction chambers 104 can be filled, for example, with solution that includes various chemicals and/or biological materials. The reaction chambers 104 may include discrete regions 106-2a and 106-2c of a light absorbing layer for converting energy from photons emitted by energy source 808 into heat energy that is then used to distribute heat by thermal conduction and/or convection within reaction chambers 104. The chamber 805 may include discrete region 106-2b for distributing heat to the chamber 805. As depicted, energy source 808 can take the form of a chip on board (COB) LED that may be well suited for distributing light evenly across a large area.

FIG. 8C also shows how in embodiments where a specific heat of the potting material is different than the specific heat of the solution within the other reaction chambers 104, the dimensions of chamber 805 may be varied. For example, in the case where a polymeric material with a lower specific heat is used to fill chamber 805, a size of the chamber 805 may be increased. Increasing the size of chamber 805 may increase the amount of the area and the potting material therein that has to be heated by the heat energy released from the discrete region 106-2b, thereby slowing a rate at which the chamber 805 increases in temperature. Increasing the dimensions of chamber 805 also increases the distance heat has to travel to arrive at temperature sensor 158, and may thereby further reduce a detected rate of temperature increase. In some embodiments and as depicted, the dimensions or composition of the discrete region 106-2b may be varied such that the discrete region 106-2b absorbs less energy than the discrete regions 106-2a and 106-2c. For example, the discrete region 106-2b may have a reduced thickness (e.g., 100 nm) when compared to the discrete regions 106-2a and 106-2c (e.g., 200 nm). In this example, the volume of material making up the discrete region 106-2b is reduced, which may in turn reduce the amount of heat that can be stored and thermally conducted into the chamber 805. As a result, the rate at which energy is able to be introduced into the chamber 805 is reduced, thereby compensating for the characteristics of a potting material of chamber 805 with a lower specific heat than reaction chambers 104. As another example, the discrete region 106-2b may be composed of a material that absorbs light energy at a reduced rate as compared to the discrete regions 106-2a and 106-2c. In some embodiments, a position of temperature sensor 158 can be varied to compensate for temperature profile differences. For example, the temperature sensor 158 may be biased away from discrete region 106-2b to reduce the heating rate measured by temperature sensor 158.

Figure 8D:
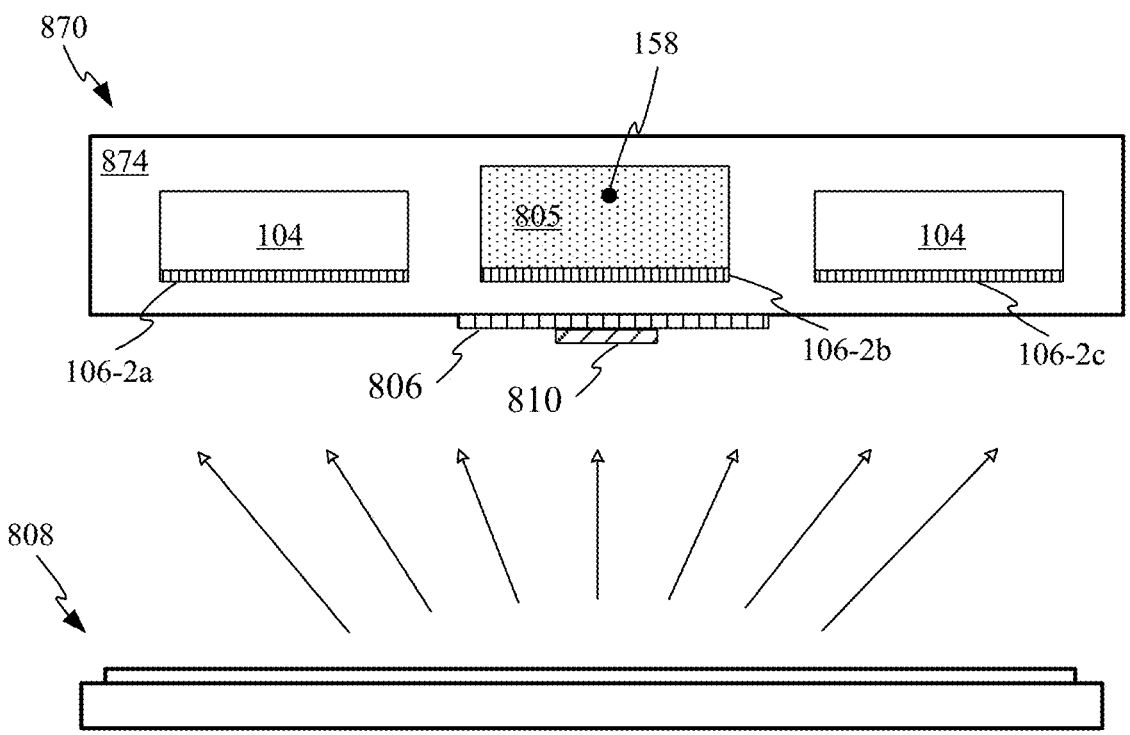
FIG. 8D shows an example reaction vessel having a light diffusion layer and a light reflecting layer.

FIG. 8D shows an example reaction vessel 870 having a light diffusion layer 806 and a light reflecting layer 810. The reaction vessel 870 may include a housing 874 defining multiple reaction chambers 104 and a chamber 805 including a potting material (e.g., a solidified polymeric material) and a temperature sensor 158 (e.g., surrounded by and fixed in place by the solidified polymeric material). The reaction chambers 104 can be filled with solution that may include various chemicals and/or biological materials. The reaction vessel 870 may include a light absorbing layer that includes multiple discrete regions 106-2a, 106-2b, and 106-2c for converting energy from photons emitted by energy source 808 into heat energy that is then distributed by thermal conduction and/or convection within reaction chambers 104. As illustrated in FIG. 8D, a position of temperature sensor 158 can be biased away from discrete region 106-2b to reduce a heating rate measured by temperature sensor 158.

FIG. 8D shows light diffusing layer 806, which as discussed above can be tuned to adjust an amount of light that reaches the discrete region 106-2b. In the illustrated example, the light diffusing layer 806 reduces the amount of light that is able to enter into housing component 874 and illuminate the discrete region 106-2b. One additional way to adjust an amount of light that reaches the discrete region 106-2b is to (alternatively or additionally) include a light reflecting layer 810 that blocks all light from passing through a region of housing 874. In some embodiments, as depicted, light reflecting layer may be positioned directly beneath temperature sensor 158, which can further reduce the amount of heat that reaches temperature sensor 158. Other configurations of light reflecting layer are also possible including a checkerboard pattern or a striped pattern that more evenly reduces the amount of light able to enter and pass through light diffusing layer 806. In some embodiments, light diffusing layer 806 and light reflecting layer 810 can be incorporated into a single layer. It should be noted that any of the depicted reaction vessels configurations can include any combination of the energy attenuating features (e.g., light diffusion layers, light reflection layers, light blocking layers, filters) illustrated in any of FIGS. 8B-8D and described in the related descriptions. Although the depicted reaction vessels display the energy attenuation features being external to the housing (e.g., referencing FIG. 8D, the light diffusion layer 806 and the light reflecting layer 810 are exterior to housing 874), the energy attenuation features may be disposed in any suitable location, including within the housing (e.g., referencing FIG. 8D, at a location within housing 874 in between the discrete region 106-2*b* and the energy source 808).

Figure 8E:
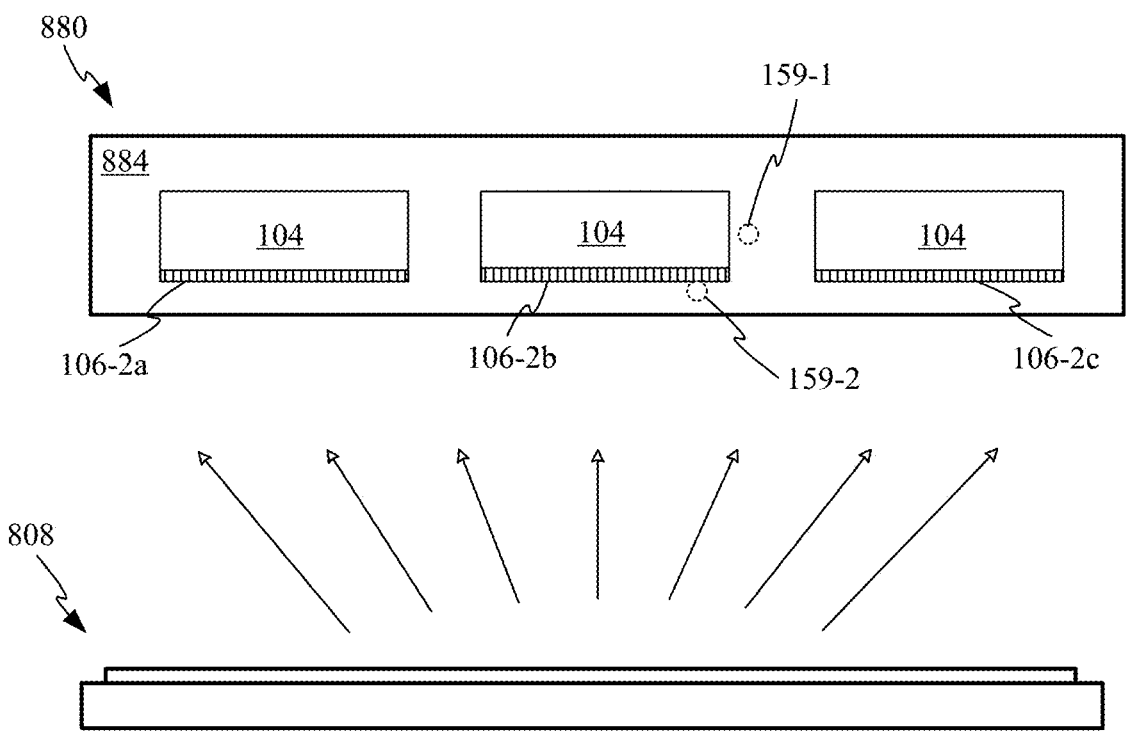
FIG. 8E shows an embodiment in which a temperature sensor can be embedded within a housing of a reaction vessel.

FIG. 8E shows an embodiment in which a temperature sensor can be embedded within a housing 884 of a reaction vessel 880. Temperature sensors can be embedded in a variety of different positions outside a chamber. For example, referencing FIG. 8E, a temperature sensor may be embedded within housing 884 at positions 159-1 and/or 159-2, as depicted. In some embodiments, a temperature sensor can be embedded at position 159-2 by adhering light absorbing layer directly atop the temperature sensor. Embedding a temperature sensor in any of these positions may allow all the depicted reaction chambers 104 to conduct normal operations since temperature sensor does not need to be within its own chamber (e.g., the chamber 805 depicted in FIGS. 8A-8D) that is filled with a potting material such as a polymeric material. Since temperature sensor 158 is not in direct contact with solution within any of reaction chambers 104, a calibration function can be applied to its readings so that temperature sensor is able to provide accurate temperature readings of solution within one of reaction chambers 104 over a predefined range of operating temperatures. In some embodiments, temperature sensors may be embedded within housing 884 by boring a hole through the housing 884, inserting the temperature sensor and associated circuitry (e.g., a conducting wire), and sealing the hole. In other embodiments, the temperature sensors may be molded directly into the housing 884.

Figure 8F:
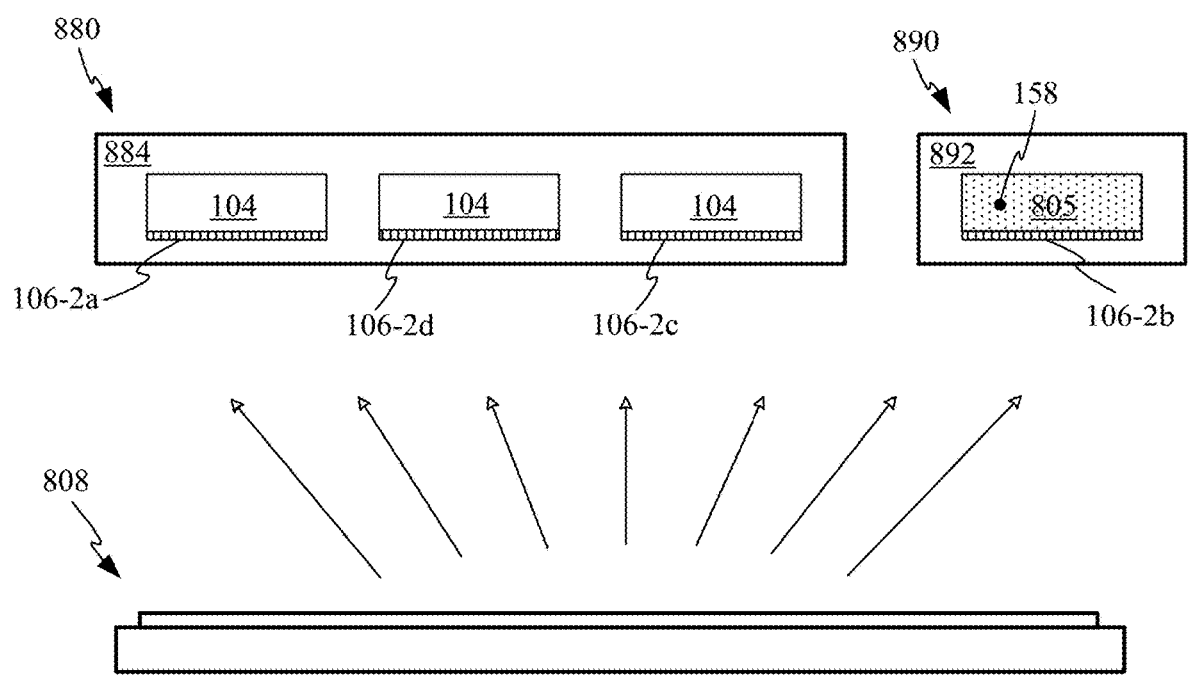
FIG. 8F shows an example embodiment in which temperature sensor is disposed within a module that is separate and distinct from a housing of a reaction vessel.

FIG. 8F shows an example embodiment in which temperature sensor 158 is disposed within a module 890 that is separate and distinct from a housing 884 of a reaction vessel 880. As illustrated, the temperature sensor 158 may be disposed within a chamber 805 of the module 890. Chamber 805 is defined by walls of a housing 892 of module 890 and can be filled with potting material as described above. In this way, vessel 890 can take the form of a separate temperature-sensing assembly. Having the temperature sensing assembly as its own module allows for the temperature-sensing assembly to be maneuvered into different positions relative to reaction vessel 880 as needed to achieve proper calibration of temperature sensor 158. For example, module 890 could be positioned closer to or farther from energy source 808 to account for differences in specific heat between the potting material surrounding temperature sensor 158 and the solution within the reaction vessels 104. Having a separate temperature-sensing assembly also allows for the temperature-sensing assembly to be replaced without having to replace or troubleshoot a temperature sensor incorporated within the much larger reaction vessel 880. As such, this modular separation may serve to reduce costs and provide for more convenient fixes to issues related to temperature monitoring. In some embodiments, reaction vessel 880 and module 890 can be coupled together (e.g., directly secured together by an attachment mechanism) to achieve a well-defined distance (e.g., as defined by an attachment mechanism) between the reaction vessels and energy source 808. In the example embodiment illustrated in FIG. 8F, the energy source 808 may direct energy toward both the reaction vessel 880 and the module 890. As such, when the energy source 808 directs energy toward the reaction vessel 880 and the module 890, the discrete region 106-2*b* of the module 890 and the discrete regions 106-2*a*, 106-2*d*, and 106-2*c* of the reaction vessel 880 may absorb the energy and thereby heat the reaction chambers 104 and the chamber 805. In some embodiments, multiple energy sources (e.g., one or more LEDS for the reaction vessel 880 and a separate LED for the module 890) may be used.

Although FIGS. 8B-8F illustrates example reaction vessels that include only one light absorbing layer, this disclosure contemplates any number of light absorbing layers (e.g., two light absorbing layers as illustrated in FIG. 8A). Additionally, any suitable number of light sources may be used (e.g., on opposing sides of the reaction vessel). Moreover, although FIGS. 8A-8F illustrate example reaction vessels with a light absorbing layer that includes multiple discrete regions, with each discrete region corresponding to one chamber, this disclosure contemplates that a single light absorbing layer may correspond to multiple chambers and further contemplates that multiple discrete regions may correspond to a single chamber.

Figure 9A:
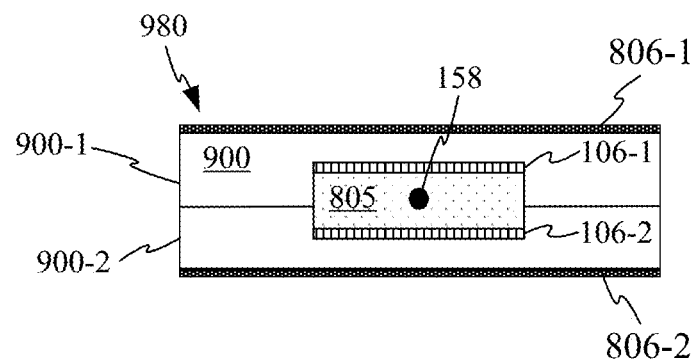
FIG. 9A shows a lateral schematic view of a cross-section of an example reaction vessel with a chamber containing a temperature sensor.

FIG. 9A shows a lateral schematic view of a cross-section of an example reaction vessel 980 with a chamber 805 containing a temperature sensor 158. In some embodiments, the temperature sensor 158 may be a thermocouple, a thermistor, a resistance temperature detector (RTD), or any other suitable sensor that may be used to determine temperature. The illustrated chamber 805 may be filled with a potting material (e.g., a cured polymeric material) as described elsewhere herein. In some embodiments, the reaction vessel 980 may be formed by forming and affixing various components of the reaction vessel 980 together. In some embodiments, housing 900 may be formed by, for example a process of injection molding. For example, a top portion 900-1 and a bottom portion 900-2 of housing 900 may be separately injection molded. In this example, both portions may have depressions that are to define reaction chambers (e.g., reaction chambers 104, which are not visible in FIG. 9A) and/or temperature-monitoring chambers (e.g., chamber 805) when the portions are secured together. Alternatively, only a first portion may have depressions, in which case the second portion may simply overlay the depressions of the first portion to create chambers. Light absorption layers (e.g., including discrete regions 106-1 and 106-2) may be adhered or plated onto the gaps such that when the top portion 900-1 and bottom portion 900-2 are secured together, the light absorption layers are long interior-facing surfaces of the resulting chambers (e.g., chamber 805 as illustrated). A temperature sensor 158 may be positioned within the chamber 805 in a desired position. In some embodiments, a polymeric material (or any other suitable potting material) may be injected into chamber 805. While the temperature sensor 158 is in the desired position, the polymeric material may be cured and solidified, such that the temperature sensor 158 is fixed in the desired position. Top portion 900-1 and bottom portion 900-2 may be secured together by any suitable means (e.g., screws, adhesives, snap-fitting). In some embodiments, as illustrated in FIG. 9A, energy attenuating features such as light diffusion layers 806-1 and 806-2 may be adhered or otherwise affixed to the housing 900 adjacent to chambers (e.g., chamber 805) with temperature sensors (e.g., temperature sensor 158).

Figure 9B:
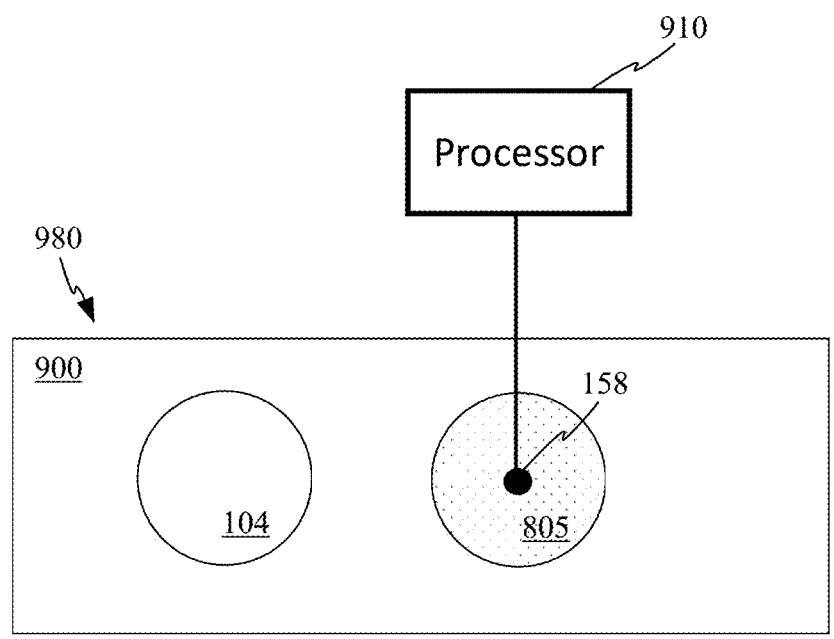
FIG. 9B shows an overhead schematic view of a cross-section of the example reaction vessel depicted in FIG. 9A with a chamber having a temperature sensor coupled to a processor.

FIG. 9B shows an overhead schematic view of a cross-section of the example reaction vessel 980 depicted in FIG. 9A with a chamber 805 having a temperature sensor 158 coupled to a processor 910. As illustrated, the temperature sensor 158 may be coupled to a processor 910 that may be configured to, among other things, determine a temperature value based on a temperature signal attracted by the temperature sensor 158. In some embodiments, a physical connection may be present between the temperature sensor 158 and the processor 910. In other embodiments, a wireless connection may be used to transmit a temperature signal from the temperature sensor 158 to the processor 910. FIG. 9B also illustrates that the reaction vessel 980 may include near the chamber 805 a reaction chamber 104, whose internal temperature may be approximated by the internal temperature of the chamber 805. In some embodiments, as illustrated in FIG. 9B, the processor 910 may be external and separate from the housing 900 of the reaction vessel. In other embodiments, the processor 910 may be within the housing 900 or affixed to the housing 900.

Figure 10:
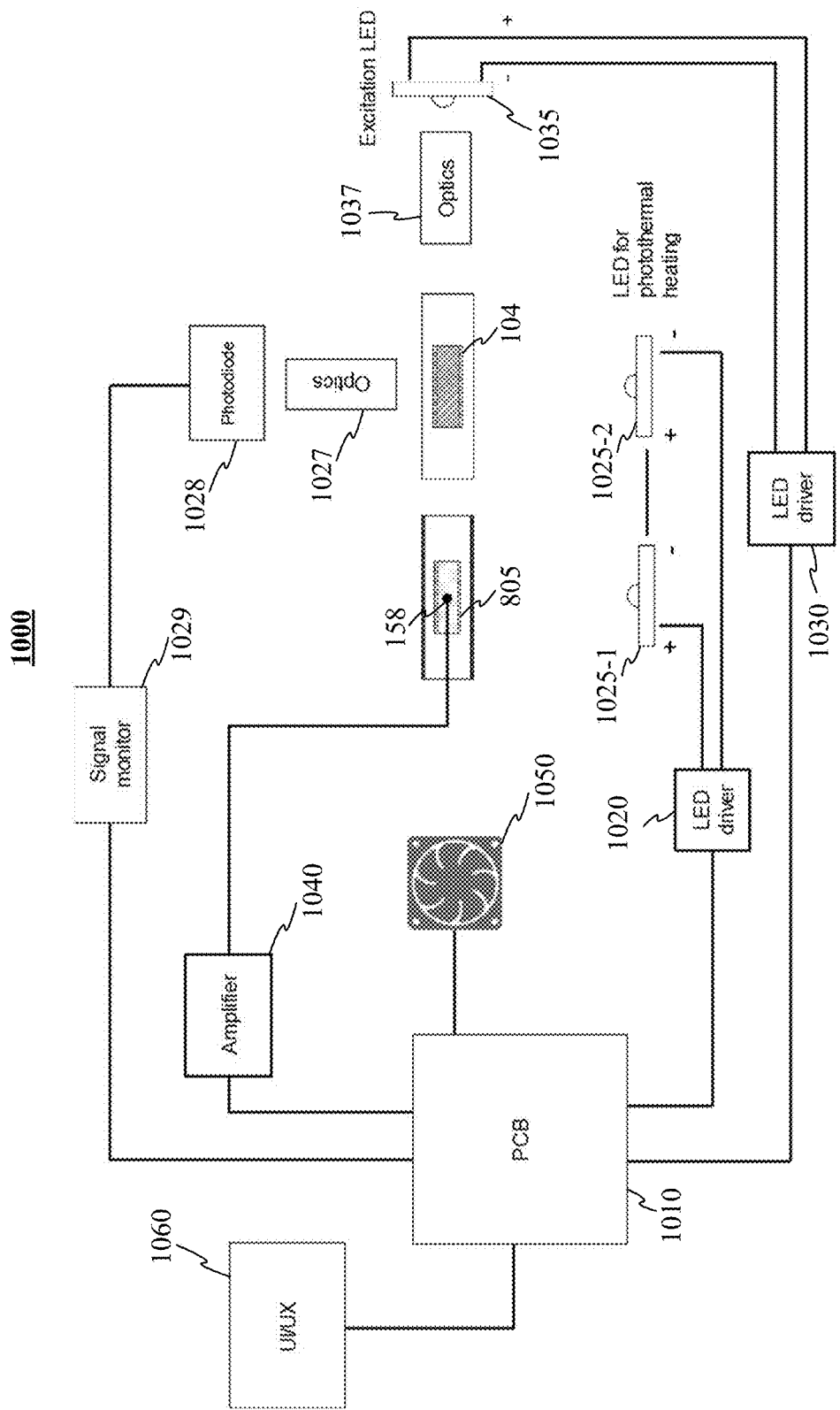
FIG. 10 shows a simplified schematic diagram of a reaction vessel system.

FIG. 10 shows a simplified schematic diagram of a reaction vessel system 1000. As illustrated, a PCB 1010 (e.g., which may include the processor 910 referenced in FIG. 9B) may interface with various elements of the reaction vessel system 1000. For example, the PCB 1010 may interface with an LED driver 1020, which may drive one or more LEDs. In the example system illustrated in FIG. 10, the LED driver 1020 drives LEDs 1025-1 and 1025-2. In this example, the LED 1025-1 is configured to direct light at a chamber 805 comprising a temperature sensor 158, and the LED 1025-2 is configured to direct light at a reaction chamber 104. The chamber 805 and the reaction table 104 may be within a housing of a reaction vessel or may be separated (e.g., the chamber 805 may be in a separate module). One or more reactions may be made to occur within the reaction chamber 104, and temperatures within the reaction chamber 104 may be regulated by adjusting the LED 1025-2. The LED 1025-1 may be adjusted along with the LED 1025-2 so that a measured temperature with the chamber 805 may be used to estimate temperature within the reaction chamber 104. The temperature sensor 158 within the chamber 805 may be coupled to the PCB 1010 (e.g., to the processor 910 described with respect to FIG. 9B, which may be within the PCB 1010). In some embodiments, as illustrated in FIG. 10, an amplifier 1040 or any other suitable circuitry may be disposed in between so as to appropriately modulate the signal from the temperature sensor 158. In some embodiments, as illustrated in FIG. 10, an LED driver 1030 may be used to drive an excitation LED 1035, which may be configured to emit an excitation light configured to cause any fluorescent markers (e.g., which may be bound to target molecules, and may thus be used as an indicator for determining the presence of the target molecules within the chamber 104 at a given time) within the reaction chamber 104 to emit a fluorescent light. The emitted florescent light may be detected by a photodiode 1028 (or any other suitable emission sensor). In some embodiments, as illustrated in FIG. 10, one or more optics (e.g., the optics 1027 and 1037) may be used to filter or otherwise modify light signals as described above. Circuitry such as signal monitor 1029 may be used to process signals from the photodiode 1028, and may transmit the resulting signal to the PCB 1010. In some embodiments, a processor within the PCB 1010 may further process the various signals it receives (e.g., from the signal monitor 1029 and the amplifier 1040) to determine outputs that may be sent to a user interface/user experience device 1060 (e.g., a display device). For example, the user interface/user experience device 1060 may receive instructions to display one or more of a temperature detected at the temperature sensor 158, an estimated temperature value of the reaction chamber 104 based on the temperature detected at the temperature sensor 158 (e.g., by adjusting the detected temperature using calibrated functions as described below), an indication of the presence and/or location of an emitted florescent signal, and any other suitable parameters or values. In some embodiments, the PCB 1010 may drive a feedback loop that is able to monitor and regulate temperatures within the reaction vessel. For example, the PCB 1010 may continuously or semi-continuously receive temperature information from the temperature sensor 158 and may adjust the LEDs 1025-1 and 1025-2 to keep temperatures within a desired temperature range. In some embodiments, the PCB may also operate a fan 1050 (or other suitable cooling device), which may be used to, for example, help cool down the reaction vessel during cool-down periods (e.g., for a step of a reaction or assay that requires a lower temperature). Although FIG. 10 illustrates some elements as being separate from the PCB 1010, this disclosure contemplates that one or more of these elements may be part of the PCB 1010. For example, the LED drivers 1020 and 1030, the signal monitor 1029, and the amplifier 1040 may reside on the PCB 1010. Although FIG. 10 illustrates particular numbers of temperature-monitoring chambers (the chamber 805), and reaction chamber (the reaction chamber 104), LEDs, emission detectors, etc., this disclosure contemplates any number of such elements (e.g., multiple chambers 805 for temperature monitoring, multiple reaction chambers 104, multiple LEDs.

Figure 11A:
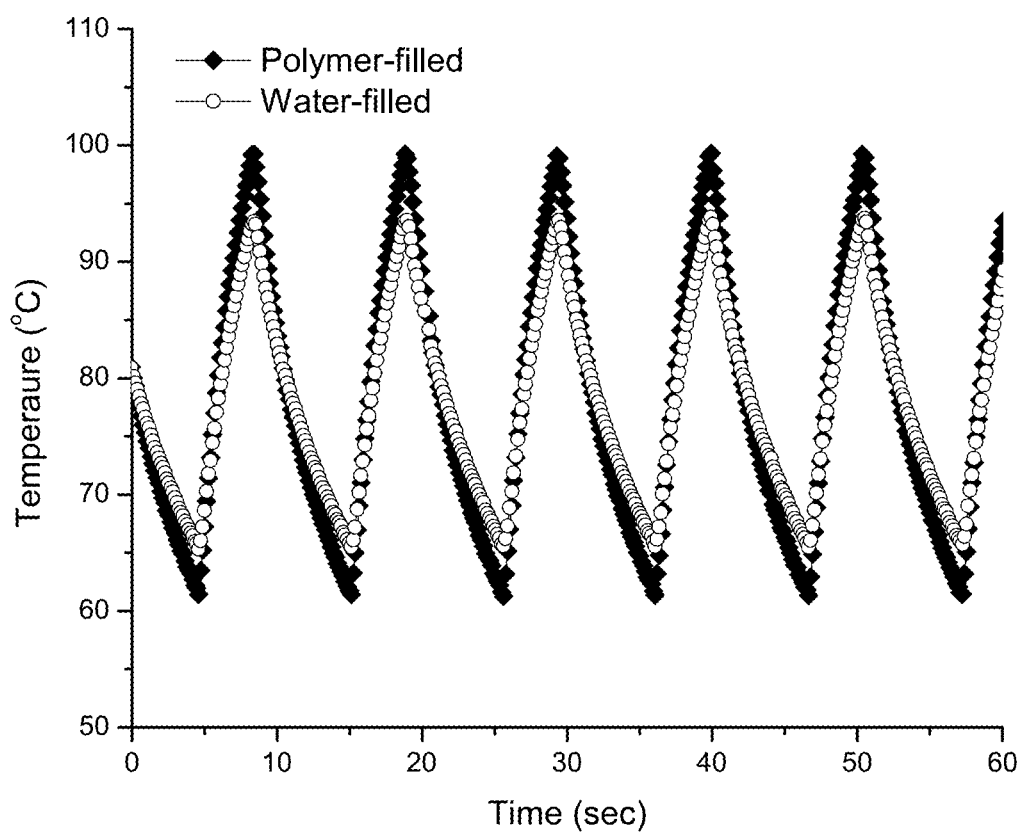
FIG. 11A shows experimental data from tests conducted on a polymer-filled chamber and a water-filled chamber.

FIG. 11A shows experimental data from tests conducted on a polymer-filled chamber and a water-filled chamber (approximating conditions of a typical reaction chamber, e.g., a water-based solution with DNA). As described above, the specific heat of the potting material (e.g., a polymeric material) within a temperature-monitoring chamber (e.g., a chamber 805, as illustrated in FIGS. 8A-8D and 8F) may not have a temperature profile that is identical to a solution within a reaction chamber (e.g., a reaction chamber 104, as illustrated in FIGS. 8A-8D and 8F). As can be seen in FIG. 11A, the temperature profiles of the polymer-filled chamber and the water-filled chamber generally track one another, but are slightly different. For example, the polymer that was tested has a lower specific heat than water, which results in the polymer-filled chamber being heated more quickly than the water-filled chamber (and cooled more quickly than the water-filled chamber). As mentioned above, a system may compensate for this temperature-profile difference by adjusting the amount of energy that is transmitted to and/or absorbed by the temperature-monitoring chamber (e.g., by varying the compositions or dimensions of the chamber or the corresponding discrete region of the light absorbing layer, by varying the light directed at the chamber, by adding energy attenuating features).

Additionally or alternatively, the system may compensate for the temperature-profile difference by calibrating the system accordingly. For example, experiments such as the one that yielded the data reflected in FIG. 11A may be performed to determine differences between a temperature-monitoring chamber and a reaction chamber. The system may then be calibrated to account for these differences. For example, the system may determine a function for converting a temperature value detected in the temperature-monitoring chamber to estimated temperature values for particular reaction chambers. In some embodiments, one or more lookup tables may be constructed for easy conversion. For example, it may be determined that a temperature of 100° C. in a particular temperature-monitoring chamber corresponds to a temperature of 97° C. in a particular reaction chamber.

Figure 11B:
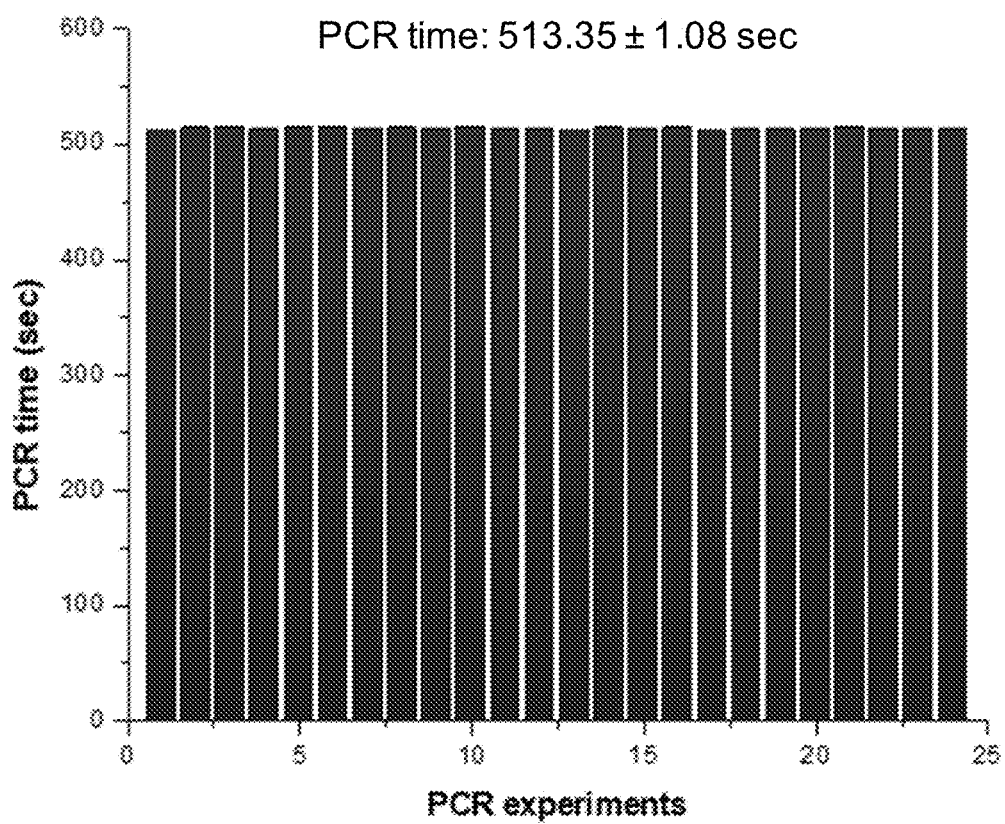
FIG. 11B shows experimental data from 24 successive PCR for 45 cycles using a polymer-filled reference chamber as a temperature-monitoring chamber with reference to which the different steps of PCR cycles were performed for all 24 successive PCR.

FIG. 11B shows experimental data from 24 successive PCR for 45 cycles using a polymer-filled reference chamber as a temperature-monitoring chamber with reference to which the different steps of PCR cycles were performed for all 24 successive PCR. In this experiment, temperature information collected from a temperature sensor within a polymer-filled chamber was used to determine when and how long to heat surrounding reaction chambers for the various PCR steps during each cycle. Twenty-four successive PCR were performed in the reaction chambers using this methodology. As reflected in FIG. 11B, the time it took to go through 45 cycles for each successive PCR remained relatively consistent, with a standard deviation of only +/−1.08 seconds. This consistency is evidence of the reliability of repeatedly using a polymer-filled chamber for monitoring temperature for a large number of successive PCR cycles. In contrast, using a water-filled chamber (where a temperature sensor was disposed within a chamber containing a water-based solution) as a temperature-monitoring chamber did not provide the same consistent and reliable results. Performing PCR cycles based on temperature information based on the water-filled chamber resulted in significant changes in PCR thermal cycling time with repeated PCR. This was at least in part because the temperature for an initial enzyme activation and denaturation temperature (e.g., which may be generally higher than 95° C.) is high enough to generate the air bubbles within the chamber, which caused inaccurate measurements of temperature. As a result, relying on such temperature measurements would result in heating and cooling steps being performed for inconsistent, non-optimal periods of time. For example, at a given time point, a temperature sensor within a water-filled temperature-monitoring chamber may incorrectly register a temperature that is below the temperature of surrounding reaction chambers. As such, based on this incorrect information, the reaction chambers may be heated for longer than necessary. As successive PCR were performed in experiments where a water-filled temperature-monitoring chamber is used as a reference, the measured temperatures would vary significantly, resulting in inconsistent times for each PCR. As shown in FIG. 11B, this is not the case with polymer-filled temperature-monitoring chambers, where each of the 24 PCR took approximately 513.35 seconds, with a standard deviation of only 1.08 seconds.

Figure 11C:
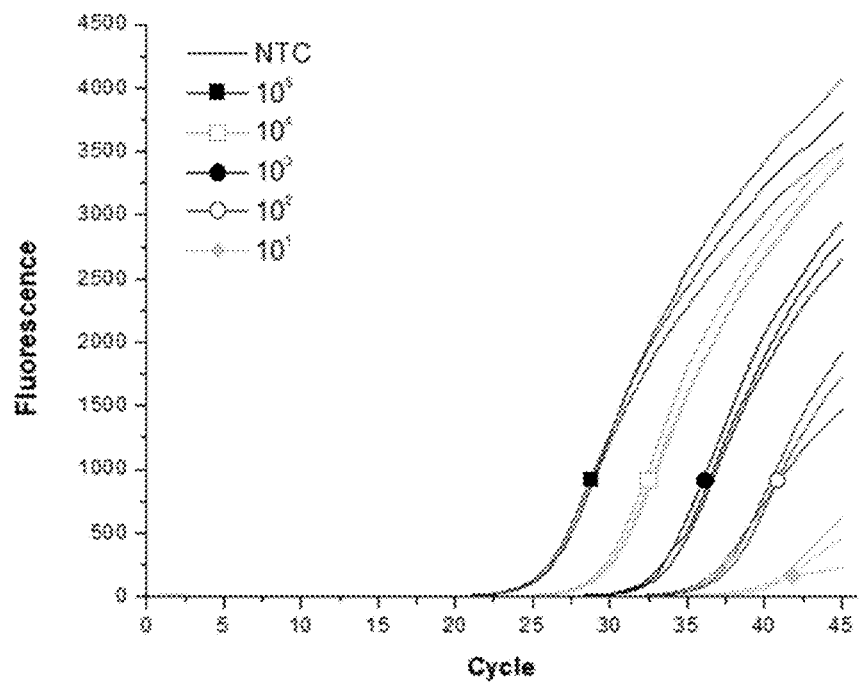
FIGS. 11C-11D show experimental data from PCR performed using a polymer-filled temperature monitoring chamber as a reference, with different initial DNA template concentrations.
Figure 11D:
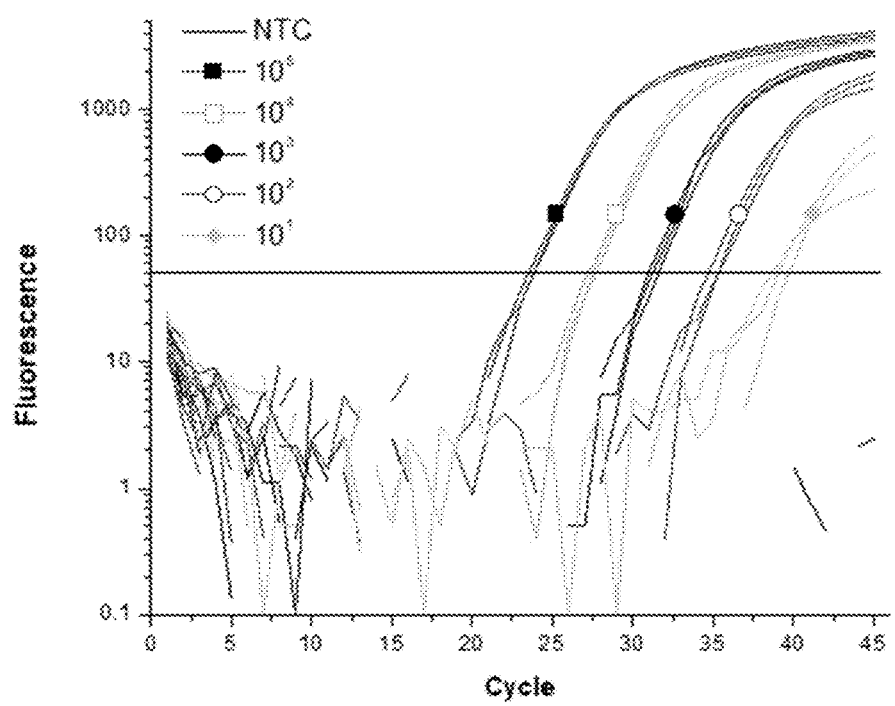

FIGS. 11C-11D show experimental data from PCR performed using a polymer-filled temperature monitoring chamber as a reference, with different initial DNA template concentrations. FIGS. 11C-11D shows detected fluorescence levels as a function of a number of PCR cycles. The experiment was performed with different initial DNA template concentrations. FIG. 11D illustrates the same data as FIG. 11C with the fluorescence values charted along a logarithmic scale. As can be seen in FIGS. 11C-11D, the experiment was conducted with initial DNA template concentrations of $10^1$, $10^2$, $10^3$, $10^4$, $10^5$, and a no template control (NTC). The NTC was merely performed as a control to prove that no increase of a fluorescence signal (as compared to background artifact signals from a fluorescent dye) would be detected without PCR amplification, and this was in the fact the case—no increase of fluorescence signal was detected for this control, as illustrated in FIGS. 11C-11D. In the experiment, PCR were performed for each initial DNA template concentration three times, as illustrated in FIGS. 11C-11D. The average of different data points such as the threshold cycle values of the different initial DNA template concentrations were compared against similar data points for conventional PCR methods, and the data was found to consistently match up. The graphs illustrated in FIGS. 11C-11D are generally similar to what the literature shows for conventional PCR with the different initial DNA template concentrations that were tested. This illustrates that the high-speed PCR enabled by the high-speed heating mechanisms of the reaction vessels disclosed herein offer high-quality results. That is, performing the different PCR steps quickly using the disclosed high-speed mechanisms does not appear to compromise the various PCR steps. The result is a much higher throughput PCR with equally robust results as the slower conventional PCR devices.

Figure 12:
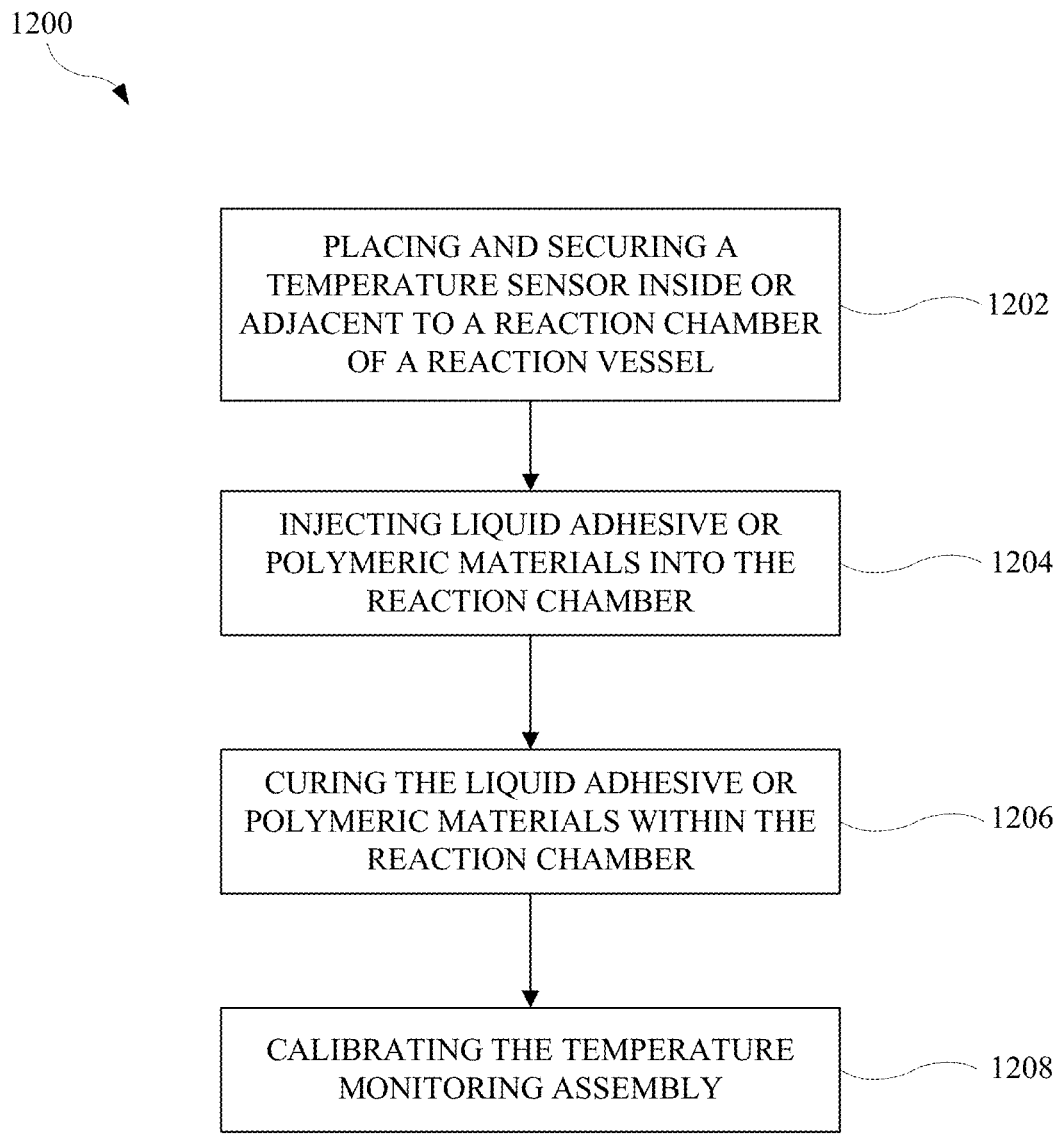
FIG. 12 shows a block diagram illustrating a method for assembling a temperature monitoring assembly.

FIG. 12 shows a block diagram illustrating a method for assembling a temperature monitoring assembly. At 1202, a temperature sensor is placed within a reaction chamber of a reaction vessel. In some embodiments, the temperature sensor can be temporarily held in place by a fixturing device that positions the temperature sensor within a central region of the reaction chamber. In some embodiments, multiple temperature sensors can be positioned within a single reaction chamber. This can be helpful in implementations where a temperature of the reaction chamber is expected to vary in different regions of the reaction chamber. At 1204, liquid adhesive or polymeric materials are injected into and fill the reaction chamber. In some embodiments, the liquid adhesive can take the form of a silane curing adhesive. At 1206, the liquid adhesive or polymeric material can undergo a curing operation that solidifies the liquid adhesive or polymeric material. The fixturing device can be released from the temperature sensor prior to or during the curing operation once a position of the temperature sensor with respect to the polymeric or adhesive material is established. At 1208, the temperature sensor can be calibrated. Calibration of the temperature sensor can be accomplished in many ways. For example, light diffusing or light reflecting layers can be placed between a light absorbing layer associated with the reaction chamber and an energy source configured to illuminate the light absorbing layer. In some embodiments, calibration of the temperature sensor can amount to creating a lookup table that correlates readings from the temperature sensor with readings taken by calibration temperature sensors that are used to monitor a temperature of solution within adjacent reaction chambers during a calibration operation. It should be appreciated that a size of the reaction chamber and position of the temperature sensor within the reaction chamber can also be adjusted at various points during the assembly operation to achieve a desired thermal profile for the temperature sensor.

Particular embodiments may repeat one or more steps of the method of FIG. 12, where appropriate. Although this disclosure describes and illustrates particular steps of the method of FIG. 12 as occurring in a particular order, this disclosure contemplates any suitable steps of the method of FIG. 12 occurring in any suitable order. Moreover, although this disclosure describes and illustrates an example method for assembling a temperature monitoring assembly, including the particular steps of the method of FIG. 12, this disclosure contemplates any suitable method for manufacturing a reaction vessel, including any suitable steps, which may include all, some, or none of the steps of the method of FIG. 12, where appropriate. Furthermore, although this disclosure describes and illustrates particular components, devices, or systems carrying out particular steps of the method of FIG. 12, this disclosure contemplates any suitable combination of any suitable components, devices, or systems carrying out any suitable steps of the method of FIG. 12.

Figure 13:
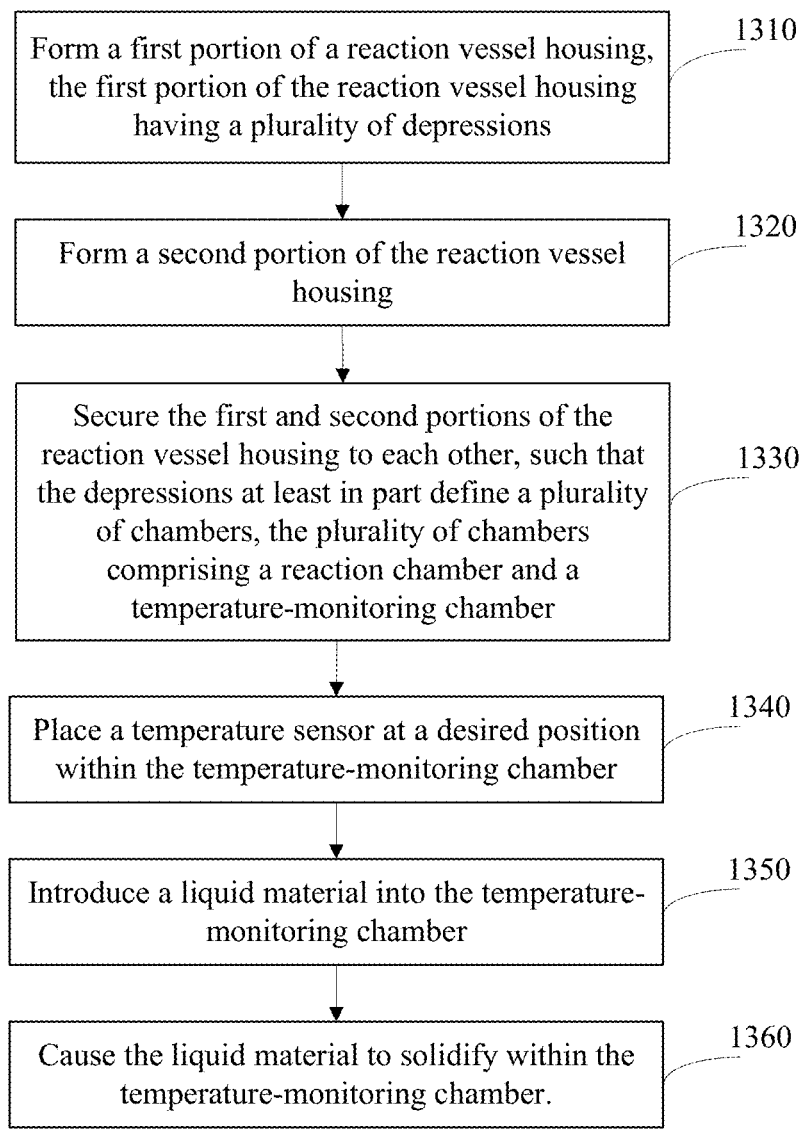
FIG. 13 illustrates an example method for manufacturing a reaction vessel.

FIG. 13 illustrates an example method 1300 for manufacturing a reaction vessel. The method may begin at step 1310, where a first portion of a reaction vessel housing may be formed, where the first portion of the reaction vessel housing has a plurality of depressions. At step 1320, a second portion of the reaction vessel housing may be formed. At step 1330, the first and second portions of the reaction vessel housing may be secured to each other, such that the depressions at least in part define a plurality of chambers, the plurality of chambers comprising a reaction chamber and a temperature-monitoring chamber. At step 1340, a temperature sensor may be placed at a desired position within the temperature-monitoring chamber. At step 1350, a liquid material may be introduced into the temperature-monitoring chamber. At step 1360, the liquid material may be caused to solidify within the temperature-monitoring chamber.

Particular embodiments may repeat one or more steps of the method of FIG. 13, where appropriate. Although this disclosure describes and illustrates particular steps of the method of FIG. 13 as occurring in a particular order, this disclosure contemplates any suitable steps of the method of FIG. 13 occurring in any suitable order. Moreover, although this disclosure describes and illustrates an example method for manufacturing a reaction vessel, including the particular steps of the method of FIG. 13, this disclosure contemplates any suitable method for manufacturing a reaction vessel, including any suitable steps, which may include all, some, or none of the steps of the method of FIG. 13, where appropriate. Furthermore, although this disclosure describes and illustrates particular components, devices, or systems carrying out particular steps of the method of FIG. 13, this disclosure contemplates any suitable combination of any suitable components, devices, or systems carrying out any suitable steps of the method of FIG. 13.

Figure 14:
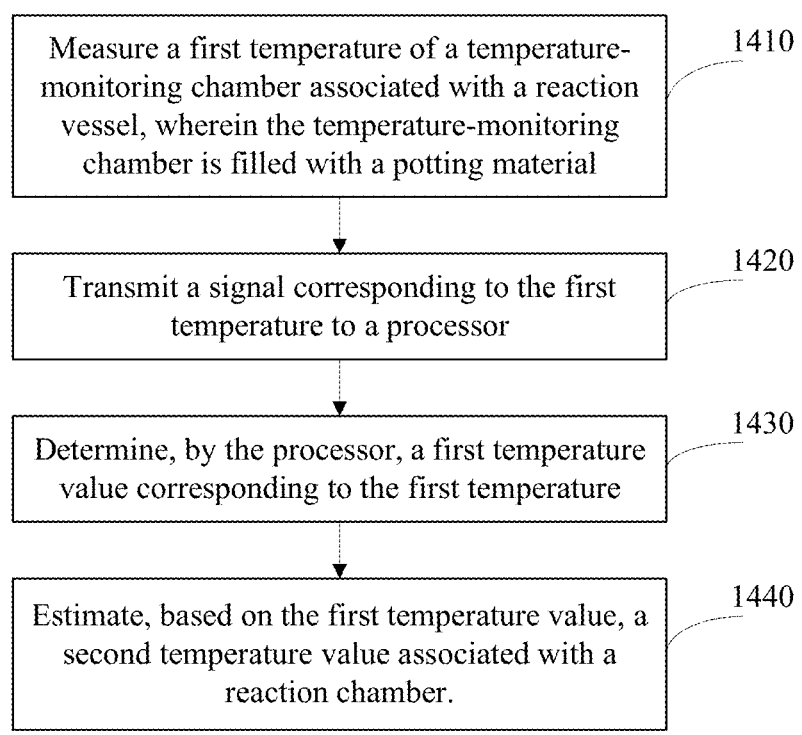
FIG. 14 illustrates an example method for monitoring a reaction chamber temperature.

FIG. 14 illustrates an example method 1400 for monitoring a reaction chamber temperature. The method may begin at step 1410, where a first temperature over temperature-monitoring chamber associated with a reaction vessel is measured. The temperature-monitoring chamber may be filled with a potting material. At step 1420, a signal corresponding to the first temperature may be transmitted to a processor. At step 1430, the processor may determine a first temperature value corresponding to the first temperature. At step 1440, a second temperature value associated with a reaction chamber may be estimated based on the first temperature value.

Particular embodiments may repeat one or more steps of the method of FIG. 14, where appropriate. Although this disclosure describes and illustrates particular steps of the method of FIG. 14 as occurring in a particular order, this disclosure contemplates any suitable steps of the method of FIG. 14 occurring in any suitable order. Moreover, although this disclosure describes and illustrates an example method for monitoring a reaction chamber temperature, including the particular steps of the method of FIG. 14, this disclosure contemplates any suitable method for monitoring a reaction chamber temperature, including any suitable steps, which may include all, some, or none of the steps of the method of FIG. 14, where appropriate. Furthermore, although this disclosure describes and illustrates particular components, devices, or systems carrying out particular steps of the method of FIG. 14, this disclosure contemplates any suitable combination of any suitable components, devices, or systems carrying out any suitable steps of the method of FIG. 14.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It will be apparent to one of ordinary skill in the art that many modifications and variations are possible in view of the above teachings.

What is claimed is:

1. A reaction vessel system, comprising:
   a first chamber filled with a first material;
   a first light absorbing region adhered to a first interior-facing surface of the first chamber;
   a second chamber filled with a second material, wherein the second material is different from the first material;
   a second light absorbing region adhered to a first interior-facing surface of the second chamber;
   a temperature sensor disposed within the second chamber for measuring a second temperature;
   one or more energy sources configured to direct light at the first light absorbing region and the second light absorbing region; and
   a processor configured to determine a first temperature of the first chamber based on the second temperature of the second chamber measured by the temperature sensor.

2. The reaction vessel system of claim 1, further comprising one or more energy attenuating features configured to reduce an amount of energy transmitted to the second light absorbing region, wherein the one or more energy attenuating features comprise a light diffusing layer, a light reflecting layer, a filter layer, or a light blocking layer.

3. The reaction vessel system of claim 1, wherein the one or more energy sources comprise a first energy source configured to direct light at the first light absorbing region and a second energy source configured to direct light at the second light absorbing region.

4. The reaction vessel system of claim 1, wherein the first material has a different specific heat than the second material.

5. The reaction vessel system of claim 4, wherein the second material comprises a polymeric material.

6. The reaction vessel system of claim 1, further comprising an excitation light source assembly and an emission detecting sensor assembly, wherein the excitation light source assembly comprises an excitation light source configured to direct an excitation light configured to cause a fluorescent marker within the first chamber to emit a fluorescent light, and wherein the emission detecting sensor assembly comprises an emission sensor configured to detect the emitted fluorescent light.

7. The reaction vessel system of claim 1, further comprising:
   a third light absorbing region adhered to a second interior-facing surface of the first chamber, wherein the second interior-facing surface of the first chamber opposes the first interior-facing surface of the first chamber;
   a fourth light absorbing region adhered to a second interior-facing surface of the second chamber, wherein the second interior-facing surface of the second chamber opposes the first interior-facing surface of the second chamber; and
   one or more additional energy sources configured to direct light at the third light absorbing region and the fourth light absorbing region.

8. A method of monitoring a reaction chamber temperature, the method comprising:

measuring a first temperature of a temperature-monitoring chamber associated with a reaction vessel, wherein the temperature-monitoring chamber is filled with a potting material;

transmitting a signal corresponding to the first temperature to a processor;

determining, by the processor, a first temperature value corresponding to the first temperature; and estimating, based on the first temperature value, a second temperature value associated with a reaction chamber within the reaction vessel.

9. The method of claim 8, wherein the temperature-monitoring chamber is housed in a module that is separated from the reaction vessel.

10. The method of claim 8, wherein the estimating comprises accessing a lookup table correlating a plurality of temperature values corresponding to the temperature-monitoring chamber with a plurality of temperature values corresponding to the reaction chamber.

11. The method of claim 8, wherein the estimating comprises applying a function to the first temperature value to generate the second temperature value.

12. The method of claim 8, wherein the potting material has a different specific heat than a material within the reaction chamber.

13. The method of claim 8, further comprising adjusting, based on the first temperature value, a power level of an energy source configured to heat the reaction chamber.

* * * * *